(12) United States Patent
Lin et al.

(10) Patent No.: US 9,803,166 B2
(45) Date of Patent: Oct. 31, 2017

(54) PRE-PROGRAMMED NON-FEEDBACK CONTROLLED CONTINUOUS FEEDING OF CELL CULTURES

(75) Inventors: Henry Lin, Newbury Park, CA (US); Jeremy Bezaire, Oak Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 745 days.

(21) Appl. No.: 14/342,304

(22) PCT Filed: Sep. 14, 2012

(86) PCT No.: PCT/US2012/055552
§ 371 (c)(1),
(2), (4) Date: Jun. 4, 2014

(87) PCT Pub. No.: WO2013/040444
PCT Pub. Date: Mar. 21, 2013

(65) Prior Publication Data
US 2014/0295545 A1    Oct. 2, 2014

Related U.S. Application Data

(60) Provisional application No. 61/535,809, filed on Sep. 16, 2011.

(51) Int. Cl.
*G01N 33/48* (2006.01)
*C12M 1/26* (2006.01)
*C12M 1/34* (2006.01)

(52) U.S. Cl.
CPC ............ *C12M 33/00* (2013.01); *C12M 41/32* (2013.01); *C12M 41/38* (2013.01); *C12M 41/40* (2013.01)

(58) Field of Classification Search
CPC .................................................... C12M 33/00
USPC ........................................................ 702/21
See application file for complete search history.

(56) References Cited

U.S. PATENT DOCUMENTS 5,629,202 A    5/1997 Su et al.

FOREIGN PATENT DOCUMENTS

| CN | 1778903 A | 5/2006 |
|---|---|---|
| DE | 102004007658 A1 | 9/2005 |
| EP | 2154244 A1 | 2/2010 |
| WO | 97/33973 A1 | 9/1997 |
| WO | 98/41611 A1 | 9/1998 |
| WO | 2004/020573 A1 | 3/2004 |
| WO | 2007/071072 A1 | 6/2007 |

OTHER PUBLICATIONS

Shizong et al., Bioreaction Engineering and Apparatus, Chinese textbook, South University of Technology Press, (Aug. 31, 2011) p. 150 (English translation).
Xingmao, Research of Metabolism Dynamics and Transcriptional Profiling of Serum-Free Fed-Batch Cho Cultures, Chinese Doctoral Master's Theses Full-Text Databases, (Sep. 15, 2009) Section 3.7 (English translation).
Dowd et al., Optimization and Control of Perfusion Cultures Using a Viable Cell Probe and Cell Specific Perfusion Rates, Cytotechnology, (2003), 42(1):35-45.
Hayter et al., The Effect of the Dilution Rate on CHO Cell Physiology and Recombinant Interferon-y Production in Glucose-Limited Chemostat Culture, Biotechnology and Bioengineering (Nov. 5, 1993) 42:1077-1085.
Maurer et al., Versatile Modeling and Optimization of Fed Batch Processes for the Production of Secreted Heterologous Proteins with Pichia Pastoris, Microb Cell Fact, (2006) 5:37 (published online Dec. 11, 2006), pp. 1-10.
Shizong et al., Bioreaction Engineering and Apparatus, Chinese textbook, South University of Technology Press, (Aug. 31, 2011) p. 150.
Xingmao, Research of Metabolism Dynamics and Transcriptional Profiling of Serum-Free Fed-Batch Cho Cultures, Chinese Doctoral Master's Theses Full-Text Databases, (Sep. 15, 2009) Section 3.7.

*Primary Examiner* — Jerry Lin
(74) *Attorney, Agent, or Firm* — Alex A. Andalis

(57) ABSTRACT

A pre-programmed non-feedback continuous feeding method based on mass balance of the substrate in the bioreactor for use in culture growth and maintenance is provided. The disclosed method does not rely on instrument, probe or operator feedback. The method provides an efficient and effective alternative to bolus feeding.

14 Claims, 20 Drawing Sheets

PRE-PROGRAMMED NON-FEEDBACK CONTROLLED CONTINUOUS FEEDING OF CELL CULTURES

CROSS REFERENCE TO RELATED APPLICATIONS

This application is a national stage application under 35 U.S.C. §371 of International Application No. PCT/US2012/055552, having an international filing date of Sep. 14, 2012; which claims priority to U.S. Provisional Application No. 61/535,809, filed Sep. 16, 2011, which is incorporated herein by reference in its entirety.

FIELD OF THE INVENTION

The instant disclosure relates to methods of feeding a cell cultures that are continuous and provide enhanced cell growth and protein expression but do not rely on feedback control to adapt to changing needs of the cell culture.

BACKGROUND OF THE INVENTION

Mammalian cell culture is widely used in the pharmaceutical and biotechnology industries for the manufacture of recombinant therapeutic proteins. The need to improve cell culture yield has increased tremendously in the last decade due to the growing market for protein therapeutics and an ongoing effort to improve production efficiency and to reduce the cost of goods manufactured. Chinese hamster ovary (CHO) cells are commonly used for the production of therapeutic proteins such as monoclonal antibodies, antigens and other specialized protein modalities.

The production of proteins using mammalian cells typically involves a fed-batch process, a process in which a nutrient supplement is fed to the cells throughout production that supports the cells' growth, metabolism and synthesis of a desired protein product. The current industry standard for cell culture fed-batch feeding processes is bolus feeding. In a bolus feeding process, nutrients are provided to the cells in intermittent discrete additions at various time points throughout the cell culture production. The bolus feeding process is simplistic in its approach, as it is confined by the practicality of manual feeding operation, which is one reason it is commonly employed.

Bolus feeding has several disadvantages, however, the foremost disadvantage being the inability to provide the precise nutrient quantities that the cells actually need. Stated another way, bolus feeding is not tailored to the specific needs of the cell culture and consequently some nutrients may be provided in higher quantities than the cell culture requires, while other nutrients may be provided at levels less than those the cells require. Thus, while simplistic in methodology, the bolus feeding approach can lead to overfeeding, which consequently leads to overflow metabolism that results in an accumulation of waste byproducts, such as lactate, that are not supportive of cell growth or biosynthesis and may actually inhibit the growth of the cells.

Another disadvantage of a bolus feeding process in a manufacturing scenario is that bolus feeding processes have inherent sources of variability that may cause differences in cell culture performance. One such source is the variability in the timing of performing the feeding operation on a required feeding day. Yet another source of variability associated with bolus feeding is the rate at which a nutrient stream is administered into the bioreactor. Separately or together, variations in the time at which feeding is performed and the rate at which the cells are fed can affect the characteristics and production of a given cell culture from run to run. Still another disadvantage associated with bolus feeding is that it is typically a manual operation that needs to be performed by an operator. The lack of automation can consume human and financial resources and represents yet another source of variability, namely subtle differences introduced into a manufacturing process due to a lack of consistency between operators or, if the operator remains the same, uncontrollable operator-introduced variation.

The disadvantages of bolus feeding can be overcome through the use of a continuous feeding process. Continuous feeding processes can be designed to better meet cellular needs by continuously feeding smaller amounts of nutrients to the culture over time, rather than in large single bolus additions. In doing so, the nutrient concentrations can be controlled and maintained at more optimal levels for cell growth, thereby preventing overfeeding, minimizing the generation of unnecessary waste products and maintaining undisrupted pseudo-steady state levels. Employing a continuous feeding, operation can also eliminate the variability in the timing and the rate of feeding associated with a bolus feeding operation, since these variables are automation controlled in a continuous feeding process. Operator intervention is also eliminated by using a continuous feeding protocol.

While others have demonstrated different forms of this approach, such approaches still introduce the possibility of operator error. For example, Hu and Europa (U.S. Pat. No. 6,156,570) demonstrated a continuous feeding strategy that improved productivity. However, this continuous feeding strategy for mammalian cell cultures relies on equipment feedback control, which can introduce variability into a feeding process.

Summarily, a drawback common to all of these methods is the fact that they all rely on some sort of instrument-obtained feedback in order to manage the process. What is needed, therefore, is a method of feeding a cell culture that can be tailored to the specific needs of a given cell culture, can be automated and does not rely on instrument-mediated feedback to control the nutrients delivered to the cell culture.

SUMMARY OF THE INVENTION

A method of continuously feeding a mammalian cell culture that does not employ feedback control is provided. In one embodiment the method comprises (a) providing a vessel comprising a mammalian cell culture comprising mammalian cells and media; (b) determining preferred values for the consumption rate ($K_1$) of a nutrient, growth rate ($K_{21}$) and growth rate ($K_{22}$) of the cell culture; (c) providing an apparatus adapted to impart a continuous feed stream to the cell culture, wherein the apparatus comprises a controller module adapted to continuously feed the culture at a flow rate F, wherein F is defined as $K_1 \exp(K_{21}t^2 + K_{22}t)$; t is the duration of time from the time the feed stream is added to the bioreactor to the time when the feed stream is stopped; and $K_1$, $K_{21}$ and $K_{22}$ are the values determined in (b); and (d) activating the controller module to initiate continuous feeding of the cell culture. In one embodiment $K_1$, $K_{21}$ and $K_{22}$ are empirically determined. In another embodiment $K_1$, $K_{21}$ and $K_{22}$ are modeled. In a further embodiment the controller module comprises a computer. In still another embodiment the feed stream comprises multiple nutrients. In a further embodiment the osmolality of the cell culture remains constant throughout the method. In another embodiment the nutrient fed to the culture is glucose. In other embodiments the mammalian cell culture is a CHO cell culture. In a further embodiment the controller module is activated in response to a preselected lactate level in the cell culture, while in another embodiment the controller module is activated in response to a preselected glucose level in the cell culture. In yet another embodiment the controller module is activated in response to a preselected level of all amino acid, such as asparagines or glutamine. In still a further embodiment the feed stream comprises two or more nutrients.

DESCRIPTION OF THE DRAWINGS

FIG. 4a is a plot showing residual glucose, FIG. 4b is a plot showing osmolality, FIG. 4c is a plot showing cell viability, and FIG. 4d is a plot showing integrated viable cell density; open circles (○) represent control with bolus glucose and feed, open squares (□) represent continuous glucose ($K_1$=0.04, $K_{21}$=−0.00015, $K_{22}$=0.0348) with bolus feed, stars (☆) represent continuous glucose ($K_1$=0.062, $K_{21}$=−0.0015, $K_{22}$=0.0288) with bolus feed, solid triangles (▲) represent continuous glucose ($K_1$=0.0504, $K_{21}$=−0.00015, $K_{22}$=0.0331) with continuous feed ($K_1$=0.59499, $K_{21}$=−0.00015, $K_{22}$=0.0348), solid diamonds (◆) represent continuous glucose ($K_1$=0.0504, $K_{21}$=−0.00015, $K_{22}$=0.0331) with constant feed (2.875 ml/hr), and solid circles (●) represent continuous glucose ($K_1$=0.0504, $K_{21}$=−0.0001.5, $K_{22}$=0.0331) with continuous feed ($K_1$=0.96678, $K_{21}$=−0.00015, $K_{22}$=0.0288).

FIG. 5a is a plot showing residual glucose FIG. 5b is a plot showing integrated viable cell density, FIG. 5c is a plot showing titer; stars (☆) represent control with bolus glucose and feed, open diamonds (◇) represent continuous glucose ($K_1$=0.105, $K_{21}$=−0.000051, $K_{22}$=0.0155) with bolus feed, open triangles (Δ) represent continuous glucose ($K_1$=0.069, $K_{21}$=−0.000048, $K_{22}$=0.018) with bolus feed, solid triangles (▲) represent continuous glucose ($K_1$=0.105, $K_{21}$=−0.000051, $K_{22}$=0.0155) with continuous feed ($K_1$=1.1320, $K_{21}$=−0.000051, $K_{22}$=0.0155), solid diamonds (◆) represent continuous glucose ($K_1$=0.105, $K_{21}$=−0.000051, $K_{22}$=0.0155) with continuous feed ($K_1$=0.8965, $K_{21}$=−0.000051, $K_{22}$=0.0155), solid circles (●) are continuous glucose ($K_1$=0.105, $K_{21}$=−0.000051, $K_{22}$=0.0155) with continuous feed ($K_1$=1.9056, $K_{21}$=−0.00006, $K_{22}$=0.0092), and solid squares (■) are continuous glucose ($K_1$=0.105, $K_{21}$=−0.000051, $K_{22}$=0.0155) with continuous feed ($K_1$=2.3821, $K_{21}$=−0.00006, $K_{22}$=0.0092).

FIG. 6a is a plot showing titer, FIG. 6b is to plot showing volumetric productivity. FIG. 6c is a plot showing viability, and FIG. 6d is a plot showing integrated viable cell density; open diamonds (◇) represent control with bolus glucose and feed (600 mL total feed), open triangles (Δ) represent continuous glucose ($K_1$=0.215, $K_{21}$=−0.000003, $K_{22}$=0.003) with bolus feed (600 mL total feed), solid triangles (▲) represent continuous glucose ($K_1$=0.215, $K_{21}$=−0.000003, $K_{22}$=0.003) with continuous feed ($K_1$=1.8774, $K_{21}$=−0.000003, $K_{22}$=0.003) (540 mL total feed), and solid diamonds (◆) represent continuous glucose ($K_1$=0.215, $K_{21}$=−0.000003, $K_{22}$=0.003) with continuous feed ($K_1$=2.0827, $K_{21}$=−0.000003, $K_{22}$=0.003) (600 mL total feed).

FIG. 7a is a plot showing titer, FIG. 7b is a plot showing volumetric productivity, FIG. 7c is a plot showing viability, and FIG. 7d is a plot showing integrated viable cell density; open triangles (Δ) represent control with bolus glucose and feed (600 mL total feed), open circles (○) represent bolus glucose with continuous feed ($K_1$=2.6503, $K_{21}$=−0.000003, $K_{22}$0.003) (600 mL total feed), and open square (□) represent bolus glucose with continuous feed ($K_1$=2.2910, $K_{21}$=−0.00003, $K_{22}$=0.003) (660 mL total feed).

FIG. 8a is a plot showing titer, and FIG. 8b is a plot showing specific productivity; open triangles (Δ) represent control with bolus glucose and feed, and open diamonds (◇) represent bolus glucose with continuous feed ($K_1$=2.7233, $K_{21}$=−0.000003, $K_{22}$=0.003) from day 4 to day 8 totaling 300 mL same volume as the control feed.

DETAILED DESCRIPTION OF THE INVENTION

Figure 1:
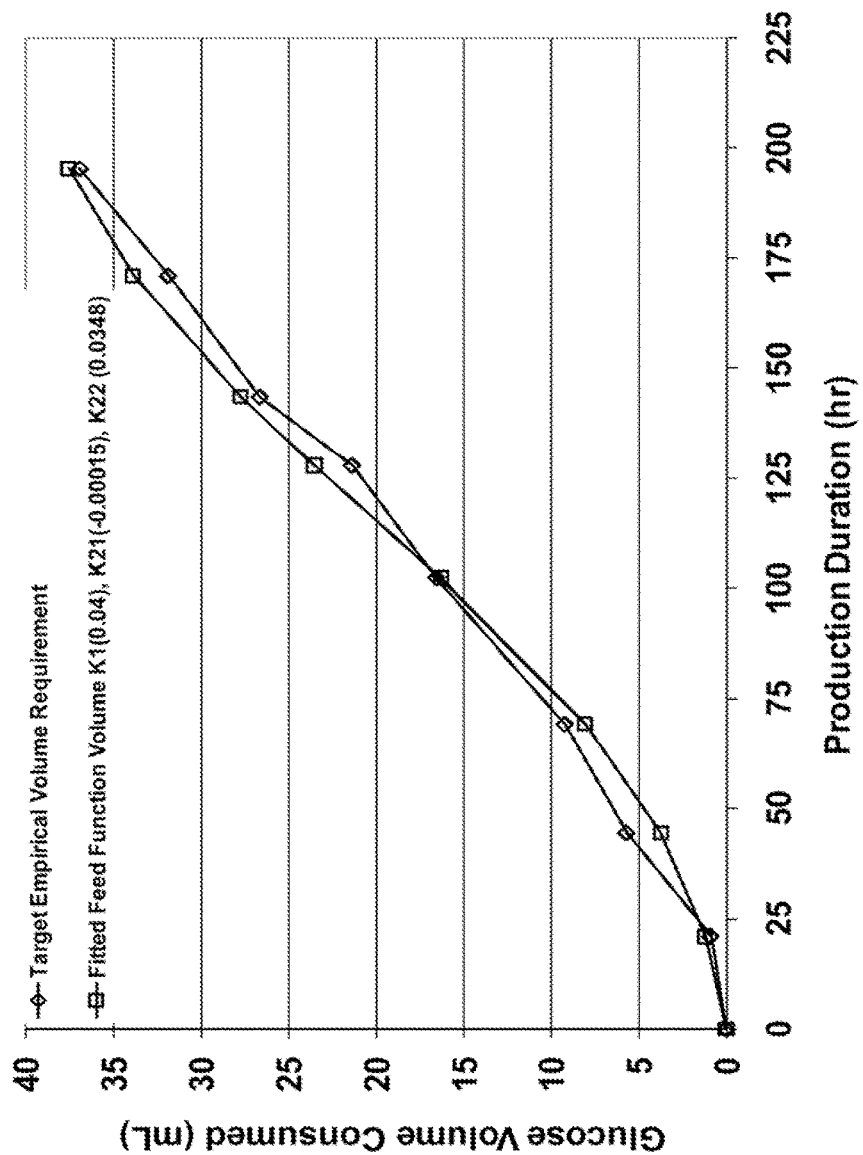
FIG. 1 is a plot showing the tightness of fit of a feeding function compared with the cell culture nutrient requirements of Cell Line 1.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present application are generally performed according to conventional methods well known in the art and as described in various general and more specific references that are cited and discussed throughout the present specification unless otherwise indicated. See, e.g., Sambrook et al., *Molecular Cloning: A Laboratory Manual*, $3^{rd}$ ed., Cold Spring Harbor Laboratory Press, Cold Spring Harbor, N.Y. (2001) and subsequent editions, Ausubel et al., *Current Protocols in Molecular Biology*, Greene Publishing Associates (1992), and Harlow & Lane, *Antibodies: A Laboratory Manual*, Cold Spring Harbor Laboratory Press, Cold Spring Harbor, N.Y. (1988), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

It should be understood that the instant disclosure is not limited to the particular methodology, protocols, and reagents, etc., described herein and as such can vary. The terminology used herein is for the purpose of describing particular embodiments only, and is not intended to limit the scope of the present disclosure.

Other than in the operating examples, or where otherwise indicated, all numbers expressing quantities of ingredients or reaction conditions used herein should be understood as modified in all instances by the term "about." The term "about" when used in connection with percentages can mean±5%, e.g., 1%, 2%, 3%, or 4%.

To meet the need for a continuous feeding method that does not rely on instrument feedback to control the process, such a feeding method is provided. In one aspect, the disclosed method is based on a model of the cell growth and substrate consumption of a cell culture. The disclosed method provides a feeding rate function with three parameters representing the specific substrate consumption rate and specific growth rate; all three parameters can be optimized for a given culture, and can be optimized for all CHO cell lines. The optimized function is used in the continuous feeding algorithm to control cell culture feeding to fit a desired profile. Such a feeding strategy can be pre-programmed and non-feedback controlled during an entire protein production process. Thus, no inputs from instruments or other forms of measurements are needed to control or adjust the feeding. It can be applied to all types of nutrient feeds, such as glucose feeds and mixture feeds. As demonstrated herein, the disclosed continuous feeding method can improve cell viability, cell density, and productivity of a given cell culture. The feeding rate function can also be tuned to achieve limited carbon feeding and thereby reduce byproduct waste, such as lactate and ammonium. The disclosed continuous feeding method is superior to bolus feeding in numerous ways, including enhanced cell culture performance, better run consistency, the elimination of feeding operation variability and the elimination of the need for manual feeding operation. This continuous feeding strategy is an improved and viable alternative to conventional bolus feeding, and reduces or eliminates the variabilities associated with the conventional bolus feeding approaches commonly employed.

In one aspect, the instant disclosure provides methods of continuously feeding a cell culture, such as a culture expressing a desired molecule. In one embodiment, the method provides a feeding function, which governs the rate and volume of nutrients provided to a growing cell culture. The feeding function can be derived as shown herein; individual variables appearing in the feeding function can all be measured for a given culture.

Broadly, the development of a feeding function for a given culture incorporates three parameters that describe the nutrient consumption and growth parameters, ($K_1$, $K_{21}$, and $K_{22}$), which are determined so as to match and satisfy the growth requirements and substrate consumption characteristics of a given cell culture. Another variable in the feeding function is the duration of the feeding, (t), which dictates the total amount of volume to be fed and can also be determined so as to match and satisfy the growth requirements and substrate consumption characteristics of the cell culture. By determining these parameters, incorporating them into a feeding function, and associating the feeding function with appropriate hardware, fully automatable continuous feeding methods, which improve performance over bolus feeding, are achieved.

The disclosed methods can be applied, to the manufacture of any protein-based molecule, such as a protein of any length, (e.g., a therapeutic protein), an antibody, a peptibody, a hemibody, a molecule comprising one or more non-naturally occurring or encoded amino acids (such as an antibody or a therapeutic protein), as peptide, an Fc fusion protein, an SCFv, a single chain antibody, etc.

The disclosed methods can also be employed on any scale desired, from bench scale (e.g., ~1, 2, 3, 4, 5, 6, 7, 8, 9, 10 or 50 liter cultures) to small scale manufacturing (e.g., ~100, 200, 300, 400, 500, 1000, 1500 or 2000 liter cultures). In a particularly desirable form, the disclosed methods can be applied at industrial scale (e.g., ~5000, 7500, 10000 or 15,000 liters). The advantages of the disclosed methods, including cost savings, will be most pronounced at the industrial scale, but are apparent regardless of the scale of production to which the methods are applied.

Any media that supports cell growth can be employed in the cell cultures and the methods of the disclosed invention. In one embodiment, the media can comprise serum, while in another embodiment the media can be serum-free. In various embodiments the media can be supplemented with one or more amino acids. In one embodiment the media is a chemically defined media.

Definitions

Following convention, as used herein "a" and "an" mean "one or more" unless specifically indicated otherwise.

The terms "polypeptide" or "protein" are used interchangeably herein to refer to a polymer comprising amino acid residues. The terms also apply to amino acid polymers in which one or more amino acid residues is an analog or mimetic of a corresponding naturally occurring amino acid, as well as to naturally occurring amino acid polymers. The terms can also encompass amino acid polymers that have been modified, e.g., by the addition of carbohydrate residues to form glycoproteins, or phosphorylated. Polypeptides and proteins can be produced by a naturally-occurring and non-recombinant cell, or polypeptides and proteins can be produced by a genetically-engineered or recombinant cell. Polypeptides and proteins can comprise molecules having the amino acid sequence of a native protein, or molecules having deletions from, additions to, and/or substitutions of one or more amino acids of the native sequence, including substitution with non-naturally occurring amino acids.

Derivation of a Feeding Function

A component of the provided non-feedback controlled continuous feeding methods is a feeding function that is tailored to the unique growth requirements and properties of a mammalian cell culture (e.g., a CHO, NS0, BHK21, PER.C6 or HEK 293 cell culture) of interest, for example a culture being grown for example for the purpose of expression a protein of interest. The feeding function incorporates the nutrient requirement profile(s) of the culture in the aim to promote growth, biosynthesis and reduce byproduct formation. In one aspect, the feeding function can be considered to be an expression of the optimal nutritional requirement(s) of the culture at any point in time over the course of a cell culture growth profile. By having an expression of the nutrition requirement(s) of a culture as a function of time (i.e., a feeding function) the need for any feedback control is eliminated, as the data that such instruments would provide is already known and incorporated into the feeding function. The feeding function also allows for fully automated operation of a cell culture growth; once the feeding formula is positioned to control the nutrient stream(s) into a bioreactor containing the cell culture and an initiation signal is provided, the entire cell growth process is controlled by the feeding function and no additional intervention is required.

The feeding function takes into account multiple variables, including the inlet flow rate of the substrate (F), the initial nutrient concentration in the bioreactor ($S_i$), the nutrient stock concentration ($S_o$), the max cell density to nutrient yield ($Y_{x/s}^m$) the specific growth rate ($\mu$), the cell density (X), and the volume of the bioreactor (V). All of these variables can be readily determined by measuring and calculating each parameter for a particular culture. The inlet flow rate of the substrate (F) is the feed rate at which the substrate is being administered to the bioreactor. The initial bioreactor nutrient concentration ($S_i$) is the concentration of the substrate at the time that the continuous feeding is going to be initiated. This can be measured with a media sample using an off-line nutrient analyzer. The nutrient stock concentration ($S_o$) is the concentration of the substrate in the liquid reservoir that the continuous feeding is administering from. The max cell density to nutrient yield ($Y_{x/s}^m$) is the peak point of total cell density divided by the total substrate consumed at that point. The cell density (X) is the viable cell density in the culture measured by a cell counter. The specific growth rate ($\mu$) is described as the rate of cell growth at a given time point divided by the viable cell density at that time point. The $\mu$ can be calculated using the relationship:

$$\mu = \frac{\ln\left(\frac{X_2}{X_1}\right)}{(t_2 - t_1)},$$

where $X_2$ and $X_1$ are the final and initial Viable cell densities, respectively, and $t_2$ and $t_1$ are the final and initial times, respectively. The volume of the bioreactor (V) consists of the total culture volume, at any given time in the bioreactor. In one embodiment the feeding function takes the form of $F=K_1\exp(K_{21}t^2+K_{22}t)$ and is derived as shown below.

The mass balance of a given nutrient in the bioreactor is described by Equation (1), where F is the inlet flow rate of the nutrient, $S_i$ is the initial nutrient concentration in the bioreactor. $S_o$ is the nutrient stock concentration, $Y_{x/s}^m$ is the max cell density to nutrient yield, $\mu$ is the specific growth rate. X is the cell density, V is the volume of the bioreactor.

$$\frac{dS}{dt} = -\frac{\mu XV}{Y_{x/s}^m} + \frac{F(S_o - S_i)}{V} \qquad (1)$$

Assuming steady state nutrient concentration in combination with continuous feeding, the equation reduces to Equation (2), $$F = \frac{q_s}{(S_o - S_i)} X_i V_i e^\mu \qquad (2)$$

where the specific nutrient consumption $$q_x = \frac{\mu}{Y_{s/x}^m}$$

and cell growth is described by $XV=X_i V_i e^m$. $X_i$ and $V_i$ are the initial cell density and bioreactor volume, respectively, at the start of the feeding. Equation (2) simplifies to Equation (3) below, $$F = K_1 e^{K_2 t} \qquad (3)$$

where $$K_1 = \frac{q_x}{(S_o - S_i)} X_i V_i \qquad (4)$$

$$K_2 = \mu \qquad (5)$$

Equation (3) is not applicable for cell culture growth beyond the exponential phase, however, since cells will enter stationary phase and then quickly into death phase. Therefore, a function for decreasing feeding once the cells are in the death phase is required. In experiments performed in the development of the disclosed method it was observed that when the specific growth rate ($\mu$) is plotted over the span of an entire production the specific growth rate $\mu$ decreases over time for CHO cells. This was found to be consistent for each of the multiple cell lines studied. Fitting a linear trend to the $\mu$ versus time shows good fit, and thus the $\mu$ can be represented by the linear equation $$K_2 = K_{21}t + K_{22} \qquad (6)$$

where $K_{21}$ is always negative, $K_{22}$ is always positive, and $|K_{22}| \gg |K_{21}|$. Substituting Equation (6) into Equation (3) generates the feeding function $$F = K_1 \exp(K_{21}t^2 + K_{22}t) \qquad (7)$$

Equation (7) forms the basis for all the continuous feeding design and experiments. Equation (7) gives curvature to the feeding profile so the trend does not just rise exponentially. Since the term $K_{21}$ is always negative, with increasing time the entire $K_{21}t^2+K_{22}t$ term can become negative and the feed trend will then decrease. $K_1$ amplifies the magnitude of the entire feeding trend as the value gets greater.

With respect to $K_1$, in Equation (4), $q_s$ is assumed to be a constant value over the entire production. $q_s$ is the specific substrate consumption rate such its for glucose. It is calculated by dividing the specific growth rate ($\mu$) by the the max cell density to substrate yield ($Y_{x/s}^m$). These terms are described above. The constant $q_s$ was studied with respect to glucose for multiple cell lines and it was observed that the assumption that $q_s$ remains constant proves to be generally true after the cells have reached peak cell density, e.g. after day 7. Thus, the assumption that $q_s$ remains constant simplifies the feeding function, and given that there are already three K variables for optimization this assumption does not greatly impact the feeding function.

While the assumption that $q_s$ remains constant is sound and does simplify the derivation of the feeding function, this assumption also removes a variable that in some cases may facilitate a more accurate feeding function. Accordingly, it is conceivable that a more accurate fit for $q_s$ could be generated. The more accurately fitted value of $q_s$ could then be substituted for $K_1$ in Equation (7) in order to derive a feeding function with even more degrees of freedom. By adding these additional degrees of freedom, it may be possible to achieve an even higher resolution feeding function. Such more accurately-fitted feeding functions form an aspect of the disclosed methods.

Derivation of a Volume Equation

As shown herein, a feeding function adapted to the unique needs of a given cell culture is provided. The feeding function describes the cell culture's nutrient needs but it does not, however, explicitly provide a term describing the total volume of a concentrated nutrient stock that will be added to a given culture. This quantity can be derived from the feeding function itself as follows.

The ability to calculate the total volume of a concentrated nutrient stock fed from the feeding function is a consideration for the use of the disclosed methods in a process development application. The knowledge of the liquid volume of a solution comprising a particular nutrient, e.g., a nutrient described by the feeding function that will be fed to a cell culture, facilitates the design of a desired feed volume, the ability to generate K values from fitting volume data, and the ability to track volume usage on the controller. Hence, calculation of the volume fed by the feeding function is a valuable parameter for the application of continuous feeding. The volume equation is derived by integrating the feeding function as shown in Equation (8).

$$\int \frac{dV}{dt} = K_1 \int e^{K_{21}t^2 + K_{22}t} \tag{8}$$

where $$F = \frac{dV}{dt} \tag{9}$$

The Maclaurin series is used to approximate the exponential term in the integral to generate a volume equation using the first five integrated terms of the series for accuracy.

$$e^x = \sum_{n=0}^{4} \frac{x^n}{n!} \tag{10}$$

where $$x = K_{21}t^2 + K_{22}t \tag{11}$$

The final volume equation is shown in Equation (12), and all the five terms of the series are used.

$$V = K_1 \left( t + \frac{K_{22}}{2} t^2 + \frac{2K_{21} + K_{22}^2}{6} t^3 + \frac{6K_{21}K_{22} + K_{22}^3}{24} t^4 + \ldots \right) \tag{12}$$

Automated Continuous Feeding Method

In many protein production processes an operator is required to monitor feedback instruments associated with a bioreactor, which acquire data about the local environment, health, cell density and protein production of a given cell culture. This data is fed back to an operator, who then adjusts growth conditions in response to the data so as to maintain a preferred set of conditions in the bioreactor.

One advantage of the disclosed methods is the ability to run the method in a fully automated fashion, thus eliminating the need tot a dedicated operator and for dedicated instruments to acquire data about the cell culture. This can translate into enhanced efficiency, cost savings in terms of human and material resources, and the ability to minimize opportunities for operator bias or error and the complete elimination of production problems associated with the failure of a feedback instrument (e.g., HPLC for amino acids, vitamins and carbon sources; glucose and lactate analyzers (Nova Profiler and YSI Instruments); cell counters (Cedex and Vi-Cell); bioreactor in situ probes (e.g., pH, dissolved oxygen, turbidity, capacitance, and NIR probes), osmometers and other instruments.

Often cell culture growth is treated as an evolving empirical exercise, with an operator continually monitoring and making adjustments to feedstock content and volumes being provided to the growing culture in response to data obtained about the status of the culture from feedback instruments. This is unnecessary when practicing the disclosed methods, as the method will be tailored to the particular cell culture and accounts for many unique properties and requirements of a given cell culture are all accounted for in the disclosed method.

The disclosed method can also provide enhanced production of a protein of interest. Since the method comprises a feeding function that has been optimized for a particular cell culture, the culture is continuously growing under conditions that maximize the health and productivity of the cell culture and consequently the cells' protein production. Thus, another advantage is the cost and resource savings the method imparts by providing maximum protein production for a given cell culture.

In one embodiment the method is performed as follows: Initially a vessel comprising a cell culture comprising cells and media is provided. As noted, the disclosed methods can be performed at any scale desired, so the provided vessel can thus also be of any scale and should be clean and sterile. For example, when working at a small scale a vessel can comprise e.g., a 1, 2, 3, 4, 5, 6, 7, 8, 9, 10, or 50 liter bioreactor; when working at a larger scale the vessel can comprise a 100, 200, 300, 400, 500, 1000, 1500 or 2000 liter bioreactor or when working at industrial scale the vessel can comprise a 5000, 7500, 10,000 or 15,000 liter bioreactor. Any vessel employed in the method can also comprise a disposable vessel, such as a flexible plastic structure adapted to serve as a bioreactor (e.g., a sterile plastic bag), or a rigid disposable plastic flask or tank.

The provided vessel is sterilized, charged with an appropriate media and a cell culture comprising cells is introduced. The cells can but need not be adapted to express a protein of interest; that is, the method can be performed on any cell culture, including a cell culture not adapted to express a particular protein of interest, or on cultures being tested or studied for a purpose other than protein production. The cells can comprise mammalian cells, such as CHO cells, and can be engineered to express a protein of interest, although the method can be performed in order to optimize production of an endogenous protein as well. In various embodiments the cells can be any eukaryotic cells, such as any mammalian cells, in particular examples the cells are CHO, NS0, BHK21, PER.C6 or HEK 293 cells. The cells can express a heterologous protein, such as an Fc-containing molecule, including an antibody or an Fc fusion protein.

When an antibody is expressed, the antibody can be derived from any species, including mouse and human, and can be a human antibody or a humanized antibody.

The cell culture introduced can comprise any number of cells. In some applications the method can be employed to enhance the growth of cells taken directly from a frozen slant, while in other application cells can be expanded to a desired amount before being introduced into the vessel.

The media on which the cells grow can be of any composition and is preferably adapted to support the growth of whichever cell culture is provided. Examples of media that can be employed in the method include MEM, DMEM, and F12 supplemented with serum or completely chemically-defined medium such as MCDB 302. See, e.g., Freshney, *Culture of Animal Cells*, 5$^{th}$ Edition, Wiley-Liss (2005) for additional exemplary media recipes that can be employed. The method can also be applied to complex medium that uses peptones and yeast extract.

Continuing with the method, preferred values for the cell culture's substrate consumption rate ($K_1$), growth rate ($K_{21}$) and growth rate ($K_{22}$) are then determined. To use the feeding function $F=K_1\exp(K_{21}t^2+K_{22}t)$, the parameters $K_1$, $K_{21}$ and $K_{22}$ can initially be determined by using a theoretical calculation. That is, these values can be determined based on extrapolation of known properties of the cells, such as the specific growth rate, max cell density to substrate yield, and the specific substrate consumption rate. These properties can be determined in prior cell culture experiments conducted on the cell line of interest or known from a review of the relevant literature. These values can serve as a starting point for further empirical development of these parameters to optimize performance.

In some cases the theoretically-calculated K values will be satisfactorily predictive and can be incorporated directly into the feeding function. In other cases it may be desirable to refine the theoretically-calculated K values using one or more test cultures and the empirical data regarding growth times, media components, nutrient requirements, feeding initiation times, etc. derived therefrom to optimize the calculated values.

To calculate initial theoretical values for $K_{21}$ and $K_{22}$, the specific growth rate ($\mu$) of a given cell culture of interest is determined using a test culture or extracted from previously known growth rates and is plotted over the course of the production time. A linear regression fit of the plot is then performed to generate the linear equation $\mu=K_{21}t+K_{22}$, wherein $K_{21}$ is represented by the slope value and $K_{22}$ is represented by the y-intercept value of the linear fit. The values determined for $K_{21}$ and $K_{22}$ are then substituted back into the feeding function $F=K_1\exp(K_{21}t^2+K_{22}t)$, leaving only the variables $K_1$ and t to be provided.

$K_1$ can be theoretically calculated using Equation (4):

$$K_1 = \frac{q_x}{(S_o - S_i)} X_i V_i \quad (4)$$

The parameter $q_s$, which appears in the calculation for $K_1$, is the specific nutrient consumption rate and is calculated from the cell culture data based on the equation $$q_x = \frac{\mu}{Y_{x/s}^m}.$$

The $q_s$ is assumed to be constant, as in the case of glucose. $X_i$ and $V_i$ are the initial cell density and initial vessel volume, respectively. $S_o$ is the stock concentration of the substrate to be fed, e.g., glucose. $S_i$ is the initial nutrient concentration in the vessel. With all these values available, $K_1$ can be readily calculated and substituted back into the feeding function.

After determining $K_1$, all three parameters $K_1$, $K_{21}$ and $K_{22}$ of feeding function F have known values. The feeding rate will change over the course of the production as a function of time, but the feeding function accounts for these transient changes and thus provides exactly the nutrients required by the culture at the exact time the culture needs them. The function can then be inputted into the controller module, which can be used to initiate, control and terminate the feeding process.

Continuing with the method, an apparatus adapted to impart a continuous feed stream to the cell culture is then provided, wherein the apparatus comprises a controller module adapted to continuously feed the culture at a flow rate F, wherein F is defined as $K_1\exp(K_{21}t^2+K_{22}t)$; t is the time from the initiation of the feeding protocol that the batch feed stream is added to the bioreactor to the end of feeding, and $K_1$, $K_{21}$ and $K_{22}$ are the values determined as described above.

Having determined $K_1$, $K_{21}$ and $K_{22}$ as described herein, an apparatus adapted to impart a continuous feed stream to the cell culture is then provided, wherein the apparatus comprises a controller module adapted to continuously feed the culture at a flow rate of F, pursuant to the feeding function. Such an apparatus can comprise a means of transferring a liquid feed stream from a reservoir to the bioreactor at a controlled rate, and a controller module capable of initiating and maintaining the flow of feed stream from a reservoir to a bioreactor according to the feeding profile. Examples of such an apparatus can comprise a Delta V controller module (Emerson, St Louis, Mo.), a controller-controlled pump (e.g., such as those available from suppliers such as Applikon Biotechnology, Foster City, Calif.; Cole-Parmer, Vernon Hills, Ill.; Watson-Marlow, Wilmington, Mass.; and SciLog, Middleton, Wis.). The pump is connected by tubing that is cell culture compatible (e.g., such as tubing available from Cole-Parmer Vernon Hills, Ill.); one end is the feed liquid vessel and on the other end is the bioreactor.

In one particular embodiment, the three K values and the feeding time t are inputted into the continuous feeding function, which has been programmed into a controller module, such as a Delta V controller module (Emerson, St Louis, Mo.). The controller module controls a pump (e.g., an Applikon bioreactor integrated pump; Applikon Biotechnology, Foster City, Calif.) connected to a feed vessel to continuously deliver the amount of feed to the bioreactor dictated by feeding function F. Depending on the particular requirements of the culture, the volume and amount of feed stream delivered to the bioreactor will change as the rate changes according to feeding function F. The controller module controls the volume of feedstock provided to the culture at any given point in time, as described in feeding formula F.

Any equipment employed to facilitate feed delivery (e.g., pump(s) and tubing) can be calibrated prior to use of the feeding formula using the pump output and measured flow rate to establish an accurate pump calibration value. This value can be used by the controller to convert the flow rates described by the feeding function F into a measure of the volume transferred by the pump. As described in the Examples provided herein, this delivery system was used for 2 L bioreactors. For larger scales such as 500 L, 2000 L and 15,000 L, the delivery system preferably, but need not, employs either mass flow controller or weight scale input. Both are established and proven equipment for feeding at large scales.

In a subsequent step of the method, the controller module is activated to initiate continuous feeding of the cell culture. When the program is initiated on the controller module the feeding commences at a predetermined point in time, with the rate of feeding (i.e., flow of nutrients from a reservoir into the vessel) changing continuously over a predetermined feeding time, as dictated by the feeding function, for a length of time described by the parameter t in the feeding function.

The trigger time point or condition at which the controller module activates the continuous feeding of the culture will depend on the nature and goals of the protein production process. In some cases a culture is provided initial nutrients at a set amount and at a subsequent point in time when the residual nutrients from the initial feedstock reaches a certain minimal target level the continuous feeding is initiated. In other cases the culture is provided no initial nutrients and nutrients are provided upon the initiation of the method, as required by the feeding function.

Additional examples of trigger conditions at which continuous feeding can be initiated include the point at which the culture reaches a designated viable cell density (VCD) or the point at which the culture reaches a designated residual byproduct level. Once one or more of these trigger conditions is established (which can be identified using a test culture before initiating the method), the observed trigger conditions can be converted to a time basis for initiating continuous feeding. That is, a test culture can be provided an initial feedstock and studied as the culture grows to determine at what time point a particular trigger condition is reached and the controller module can be set to activate the feeding function at that point in time.

One specific example of a residual nutrient that can be monitored is glucose; the time point at which initial glucose levels drop to a level no longer sufficient for cell growth can serve as a trigger condition or time point for the controller module to initiate continuous feeding.

In another example, viable cell density can be used as a trigger condition. In one particular example, a viable cell density target is ~5×10$^6$ cells/mL, which corresponds to the point at which the cells are just entering the exponential phase.

In still another example, byproduct accumulation levels can be used as a trigger condition. In one specific example, the accumulation level of the byproduct lactate to greater than ~0.5 g/L can serve as a trigger condition which, when met, initiates continuous feeding in order to maintain the low lactate by preventing overfeeding.

Optimizing the Feeding Function

As stated herein, theoretical values for $K_1$, $K_{21}$ and $K_{22}$ can be calculated to provide initial values, but in another aspect of the disclosed methods the calculated values can optionally be optimized. In order to optimize the $K_1$, $K_{21}$ and $K_{22}$ values, a "design of experiments" (DOE) approach can be applied to evaluate a given range for each of the three $K_1$, $K_{21}$ and $K_{22}$ parameters. The ranges are determined based on the performance observed in an initial culture in which the theoretical values of $K_1$, $K_{21}$ and $K_{22}$ were used in the feeding function. The ranges tested in the optimization process are also guided by the total amount of substrate volume desired to be fed (which can be determined as described above using Equation 12).

A fourth parameter that appears in a feeding function that can be optimized is the total feeding time (t). Once the t in the feeding function reaches the total run time, the feeding should stop. The total run time is used to balance the total substrate volume to be fed to the culture with the duration that a culture needs to be fed. For example, if it is desired to feed a culture over a longer span of time but using less total feed, in the feeding function t can be increased and the $K_1$ can be decreased.

In one embodiment an empirical method can be employed to calculate $K_1$, $K_{21}$ and $K_{22}$ values. An advantage to obtaining the initial $K_1$, $K_{22}$ and $K_{22}$ values empirically rather than theoretically is that an empirical approach can generate more accurate values, which leads to enhanced performance and protein production when the method is employed.

In another aspect, in order to better determine $K_1$, $K_{21}$ and $K_{22}$, the volumetric substrate consumption rate (g/hr) for a culture is calculated first, using data based on actual bolus feeding production data. The volumetric substrate consumption rate is determined by running a test culture comprising the cells that will be used in the method and monitoring substrate consumption using a standard cell culture nutrient analyzer (e.g., Nova Profiler or an analyzer such as those manufactured by YSI Instruments including the model YSI 7100, YSI 1500, YSI 5300, YSI 2300 and YSI 2700 analyzer units). A dilution factor is then applied to the substrate consumption rate, which is determined based on the known properties of vessel volume and substrate stock concentration, to convert it into the substrate feeding rate that is required to deliver the amount of substrate that is required by the culture. The calculated substrate feeding rate is then plotted over the course of the production time. The feeding function, $F=K_1\exp(K_{21}t^2+K_{22}t)$, is then used to best fit this plot. This process generates the best fit values for $K_1$, $K_{21}$ and $K_{22}$. Optionally, these values can then be used as a starting point for further optimization of the performance using a DOE approach or a simple single factor approach.

Additional Optimization Approaches

The continuous feeding function can be derived based on the mass balance of a particular nutrient within the cell culture system. In this approach a cell growth model is integrated into this derivation to solve for the feeding function. In one example, a linear specific growth rate model can be used in such a derivation. This provides the feeding function, $F=K_1\exp(K_{21}t^2+K_{22}t)$. This feeding function is used to perform continuous feeding of nutrients in cell culture for example, glucose, amino acids, etc. In this equation F is the nutrient flow rate, t is the elapsed time of the culture, $K_1$ is a parameter describing the substrate consumption, and $K_{21}$ and $K_{22}$ both describe the growth profile of the culture.

This is not, however, the only way in which a continuous feeding function can be generated. In another approach, rather than using a linear specific growth rate model as described above, a sigmoidal model can be used instead to describe the specific growth rate of the culture. The sigmoidal specific growth rate model will generate a different feeding function from that generated using a linear specific growth rate model. This sigmoidally-derived feeding function will work equally as well as the linearly-derived feeding, function, as long as its defined parameters are optimized for every cell line.

In still another example for deriving a feeding function, rather than using a linear or a sigmoidal equation form to model specific growth rate, the cell growth curve can be modeled instead to generate an empirical feeding function that matches the growth profile. Such feeding function would be a polynomial of the second order or higher, depending on the goodness of fit. Thus, a feeding function can be optimized using a linear or sigmoidal function to model for specific growth rate, or an entirely new feeding function can be derived based on polynomial fit to the growth or nutrient curve, and the choice of which function to use can be based on a consideration of any number of factors, including simplicity of equation for development use, need for enhanced degrees of freedom to manipulate the feeding profile or improved accuracy with direct fit to actual cell growth or nutrient consumption profile.

Feeding Function for Feeds Containing Multiple Nutrients

The disclosure supra has, in one aspect, been directed to feeding functions comprising a single nutrient, or a feedstream comprising a mixture of nutrients in which only one of which is accounted for in the feeding function. The disclosed methods are not limited to a single nutrient, however, and can be applied to multiple nutrient streams or a feed stock comprising multiple nutrients. The disclosed methods can be readily adapted to incorporate a feeding function that accommodates two or more nutrients, although a different approach is taken when performing continuous feeding using a mixed substrate feed.

When a feedstream comprising multiple nutrients is employed it is difficult to calculate specific $K_1$, $K_{21}$ and $K_{22}$ values for the entire mixture. One approach to describing multiple nutrients in a single feedstream is to select a single substrate in the feed to follow to generate the data needed to generate initial $K_1$, $K_{21}$ and $K_{22}$ values for the mixed nutrient feedstream. For example, when using a feedstream comprising glucose and other nutrients, only the glucose component of a complex feed stream can be selected to be monitored. Data obtained from the metabolism of the glucose component of the stream (e.g., consumption rate as a function of time) can be used to generate $K_1$, $K_{21}$ and $K_{22}$. Generally, it is preferable to follow a substrate that is highly utilized or essential for cell growth, viability and production.

The initial K values are then optimized for the entire feed mixture. Because the feed contains multiple substrates at various concentrations, empirical testing is preferred for achieving, the optimal performance. In addition to optimizing the feeding function for multiple substrates, growth media can be developed to adjust nutrient concentrations that best lit the continuous feeding rate.

EXAMPLES

The following examples, including the experiments conducted and the results achieved, are provided for illustrative purposes only and are not to be construed as limiting.

Materials and Methods

Cell Lines

Three cell lines, Cell Line 1, Cell Line 2 and Cell Line 3, each encoding a different monoclonal antibody, were studied. Cells were passaged in shake flasks (Corning, N.Y.) on a 3-4 day schedule, after thawing and supplemented with 100 µg/L IGF-1 (SAFC Biosciences, Lenexa, Kans.) and 500 nM MTX (Bedford Laboratories, Bedford, Ohio). The passage conditions were 36° C., 5% $CO_2$, and 160 rpm for 125 mL and 500 mL flasks and 90 rpm for 3 L flasks using a shaker platform from Thermo Electron Corporation, Waltham, Mass.

Cell Line 3 cells were used to inoculate the N-1 vessel at $0.75e^6$ cells/mL. The N production vessel was inoculated at $1.0e^6$ cells/mL for Cell Line 1 and for the first Cell Line 2 experiment testing continuous feeding. Then the subsequent Cell Line 2 and Cell Line 3 experiments were inoculated at $1.4e^6$ cells/mL. Production duration varied for the different cell lines as described in the Results and Discussion section.

Bolus feedings strategies varied between the cell lines. The feed volume and feed days are described in detail in the Results and Discussion section below. Bolus glucose feed was fed daily to 6 g/L starting on the second day.

Analytical Techniques

VCD and viability were measured on a CEDEX instrument (Innovatis, Germany) and metabolites on the NOVA BioProfile 100+ (NOVA Biomedical, Mass.). pH and gases were analyzed on the Bioprofile pHox (NOVA Biomedical, Mass.) and osmolality on the osmometer (Advanced Instruments, Norwood, Mass.).

Titer was measured by reverse-phase HPLC analysis. The analysis utilized affinity chromatography, wherein Protein A was immobilized on a column support. At neutral pH, monoclonal antibody (mAb) molecules were hound to the Protein A through the Fc region while host-cell proteins, conditioned media components and buffer were eluted from the column in the flow-through. Captured mAbs were eluted at acidic pH and detected by UV absorbance at 280 nm. A calibration curve was derived from a universal mAb standard and the corresponding peak areas using linear regression analysis. Concentrations of the mAb in the test samples were then calculated from the calibration curve and the ratio of the extinction coefficients from the universal mAb standard and the mAb tested.

Results and Discussion

Comparison of the Continuous Feeding Method to the Bolus Pealing Method

Cell Line 1 was used as the first model cell line to test the continuous feed function $F=K_1 \exp(K_{21}t^2+K_{22}t)$ and to study how cell culture performance compared with cell culture performance using bolus feeding. One objective was to demonstrate the application of the continuous feeding model as a viable substitute for cell culture fed-batch. The ability to use the feed function to continuously feed glucose and maintain the concentration within a defined range was another objective and an improvement over manual bolus glucose feeding.

A bolus process studied for Cell Line 1 was a 13 day production process. Bolus glucose was added daily up to 6 g/L. Bolus feeds were added on days 5, 7 and 9 at the volume of 138 mL each totaling 414 mL of feed.

To apply the feed function, the K values need to be determined. Using a theoretical approach, the $K_1$ value can be approximated by Equation (4) using the specific glucose consumption rate, and the initial glucose, viable cell density and culture volume levels at the start of feeding. $K_{21}$ and $K_{22}$ values can be approximated by thong a linear line to the specific growth rate time course of the cell line, where $K_{21}$ is the slope and $K_{22}$ is the y-intercept.

Although the theoretical approach to determining $K_1$, $K_{21}$ and $K_{22}$ was initially favored for its ease and simplicity, it was ultimately decided to pursue an empirical approach, which provides more accurate K values. Using the empirical approach, K values were determined by fitting the feed function F to match the actual glucose consumption volume data generated from bolus feeding runs. FIG. 1 graphically illustrates one example how the feeding function volume equation fits closely the empirical glucose volume consumption data curve. For this data set, the goodness of fit generated K values of $K_1$=0.04, $K_{21}$=−0.00015, and $K_{22}$=0.0348, Hence this set of K values was used as one condition for testing. Similarly, different sets of K values were also generated by fitting the feed function volume equation to other bolus feeding runs' glucose data.

Figure 2:
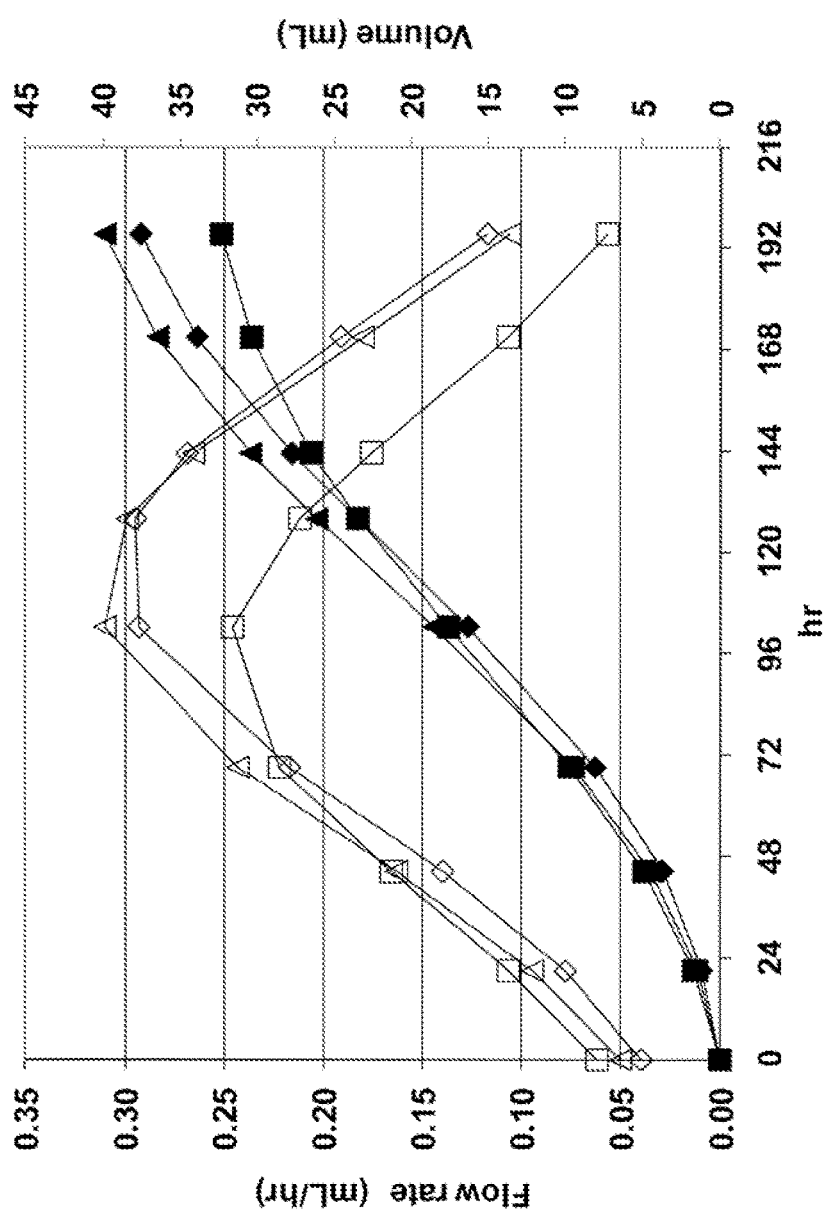
FIG. 2 is a plot depicting the glucose continuous feeding rate and volume accumulation trends tested for Cell Line 1; open shapes are glucose flow rates and shown on the left Y-axis and solid shapes are cumulative glucose volume fed and shown on the right Y-axis; open triangles (Δ) and solid triangles (▲) are the continuous glucose flow rate and volume accumulation, respectively, for $K_1$=0.0504, $K_{21}$=−0.00015, $K_{22}$=0.0331, while open diamonds (◇) and solid diamonds (◆) are the continuous glucose flow rate and volume, respectively, for $K_1$=0.04, $K_{21}$=−0.00015, $K_{22}$=0.0348, and open squares (□) and solid squares (■) are the continuous glucose flow rate and volume, respectively, for $K_1$=0.062, $K_{21}$=−0.00015, $K_{22}$=0.0288.

Several sets of K values that best fit the glucose consumption volume curve were selected for evaluation. FIG. 2 shows three continuous glucose feed functions tested for Cell Line 1. The K values for each feed function are described in the legend. Each of the feed functions generates a different flow rate profile and a different total glucose volume added. These were empirically tested to see which best maintains glucose concentration consistently within a range throughout production.

Figure 3:
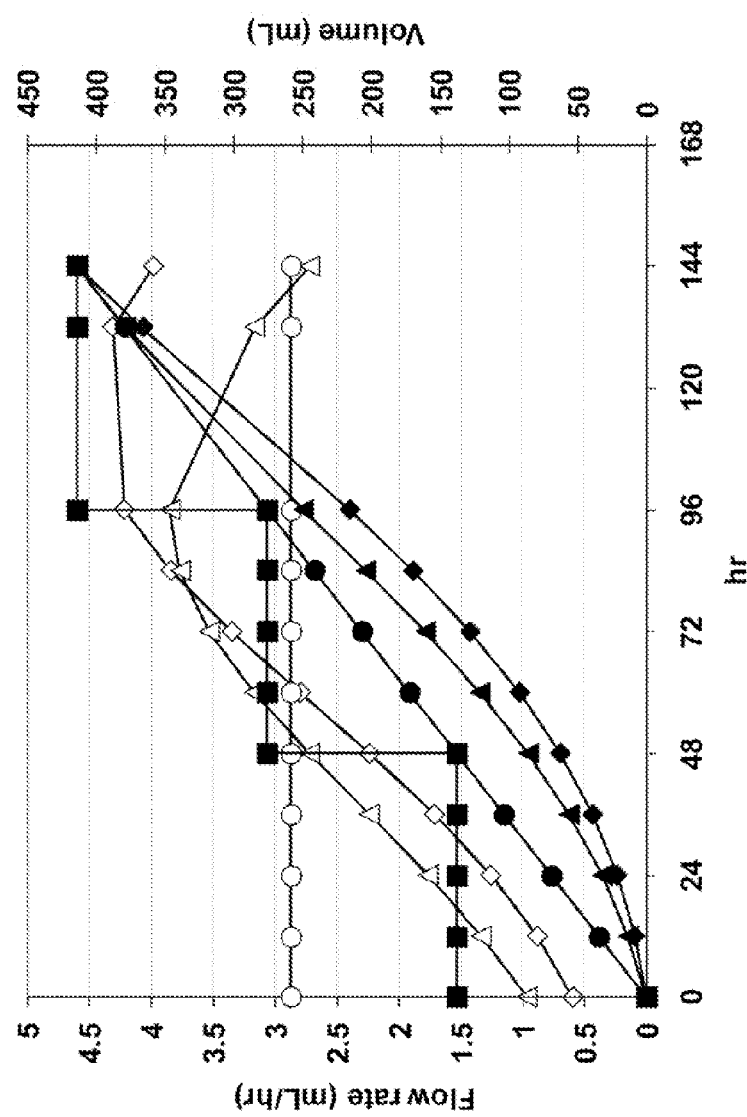
FIG. 3 is a plot depicting the feed flow rate and volume accumulation trends tested for Cell Line 1; open shapes are feed flow rates and shown on the left Y-axis and solid shapes are cumulative feed volume fed and shown on the right Y-axis; open diamonds (◇) and solid diamonds (◆) represent the continuous feed flow rate and volume, respectively, for $K_1$=0.59499, $K_{21}$−0.00015, $K_{22}$=0.0348, while open triangles (Δ) and solid triangles (▲) represent the continuous feed flow rate and volume, respectively, for $K_1$=0.96678, $K_{21}$=−0.00015, $K_{22}$=0.0288, open circles (○) and solid circles (●) represent the constant feed flow rate of 2.875 ml/hr and its cumulative volume, respectively, and solid squares (■) represent the cumulative volume trend of the control bolus feed.

Three different continuous nutrient mixture feeding profiles were also tested in combination with one of the continuous glucose feeding ($K_1$=0.0504, $K_{21}$=−0.00015, $K_{22}$=0.0331) described above. One was a constant continuous feed rate of 2.875 mL/hr evaluating a linear volume delivery profile on cell culture performance. The other two continuous feeds utilized the feed functions which are exponential by nature (FIG. 3). The K constants for these two continuous feed runs were derived simply by using the same $K_{21}$ and $K_{22}$ values of the other two continuous glucose feeding runs described in FIG. 1, and back calculating the $K_1$ to match the total volume of 414 mL to be fed over the span of day 5 to day 9. These K constants tested serve only as a starting point for evaluating the K values in the feed function. These continuous feed runs were compared to the standard bolus feeding run as shown in FIG. 3. The bolus feeds were administered three times at 138 mL each. All four feed strategies were designed to deliver the same total volume of 414 mL at the end of production. Therefore, any differences in cell culture performance would only be attributed to the different feeding strategy trends and not the volume fed. Summarily there were runs using two continuous feeding streams, one of the glucose and the other of the nutrient mixture. One condition was a constant flow rate continuous feeding of the nutrient mixture paired with a continuous glucose feeding using the feed function. The other two were two different continuous nutrient mixture feedings paired with the same continuous glucose feeding as the constant flow above. The fourth was the standard bolus glucose and bolus nutrient mixture feed run.

FIG. 4 shows the results for the continuous feed model applied to Cell Line 2. The data in FIG. 4a demonstrates that continuous glucose feeding could successfully maintain the residual glucose concentration consistently within a defined range of glucose concentrations. The run represented by solid circles (●), is a run with dual continuous glucose ($K_1$=0.0504, $K_{21}$=−0.00015, $K_{22}$=0.0331) and feed ($K_1$=0.96678. $K_{21}$=−0.00015, $K_{22}$=0.0288). The glucose concentration range of this run was maintained between 2-4 g/L. The bolus glucose, represented by open circles (○) showed the expected and typically-observed oscillatory pattern as a result of manual feeding to 6 g/L every day. Other continuous glucose runs accumulated higher glucose over time or ended with lower glucose. The results shown in FIG. 4a demonstrate that the feed function can be empirically optimized to achieve the desirable consistent glucose level throughout production. Summarily, it was observed that continuous glucose feeding maintained the glucose concentration in the culture within a set range in a automated way, whereas the bolus glucose created oscillatory behavior, and not the stable consistent profile desired.

Figure 4A:
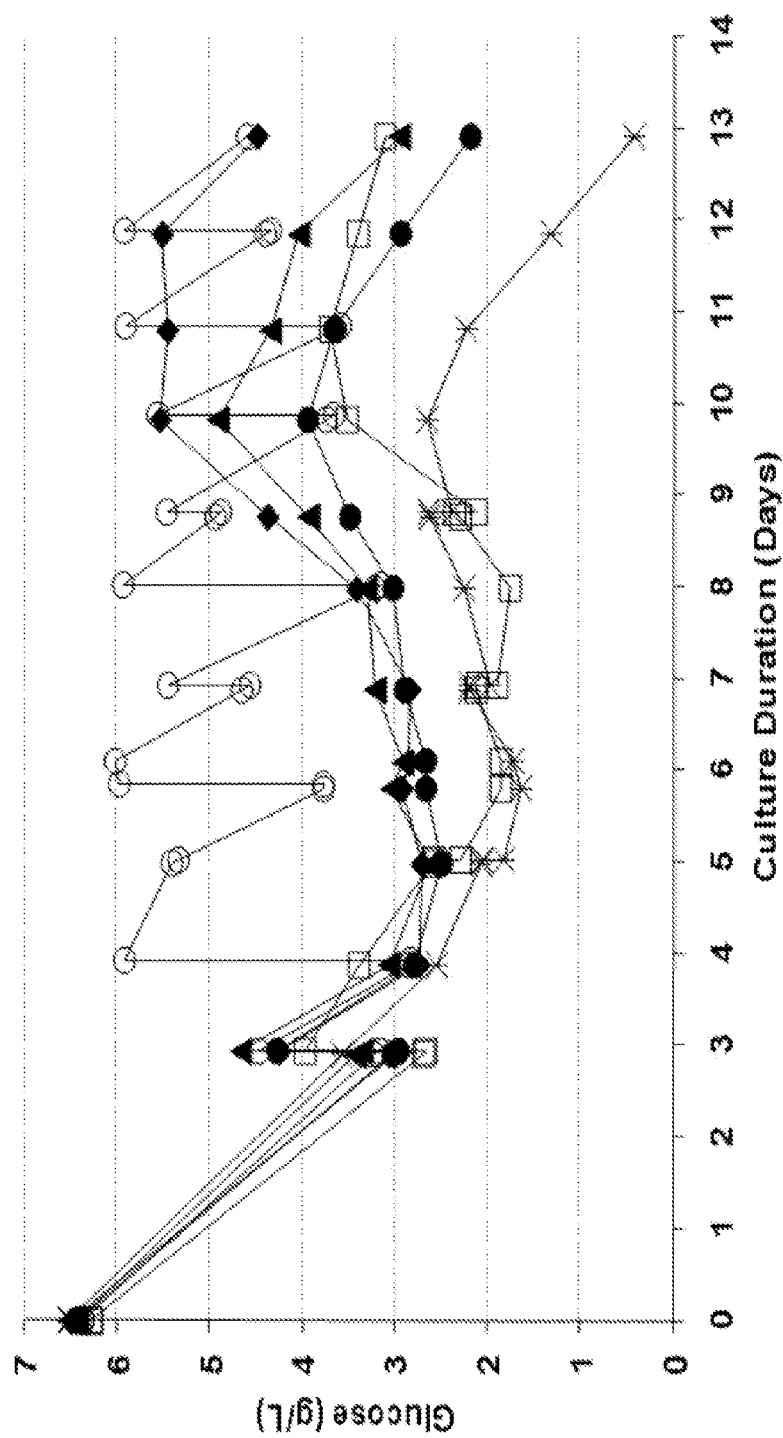
FIGS. 4a-4d are a series of plots related to experiments involving Cell Line 1, and more particularly
Figure 4B:
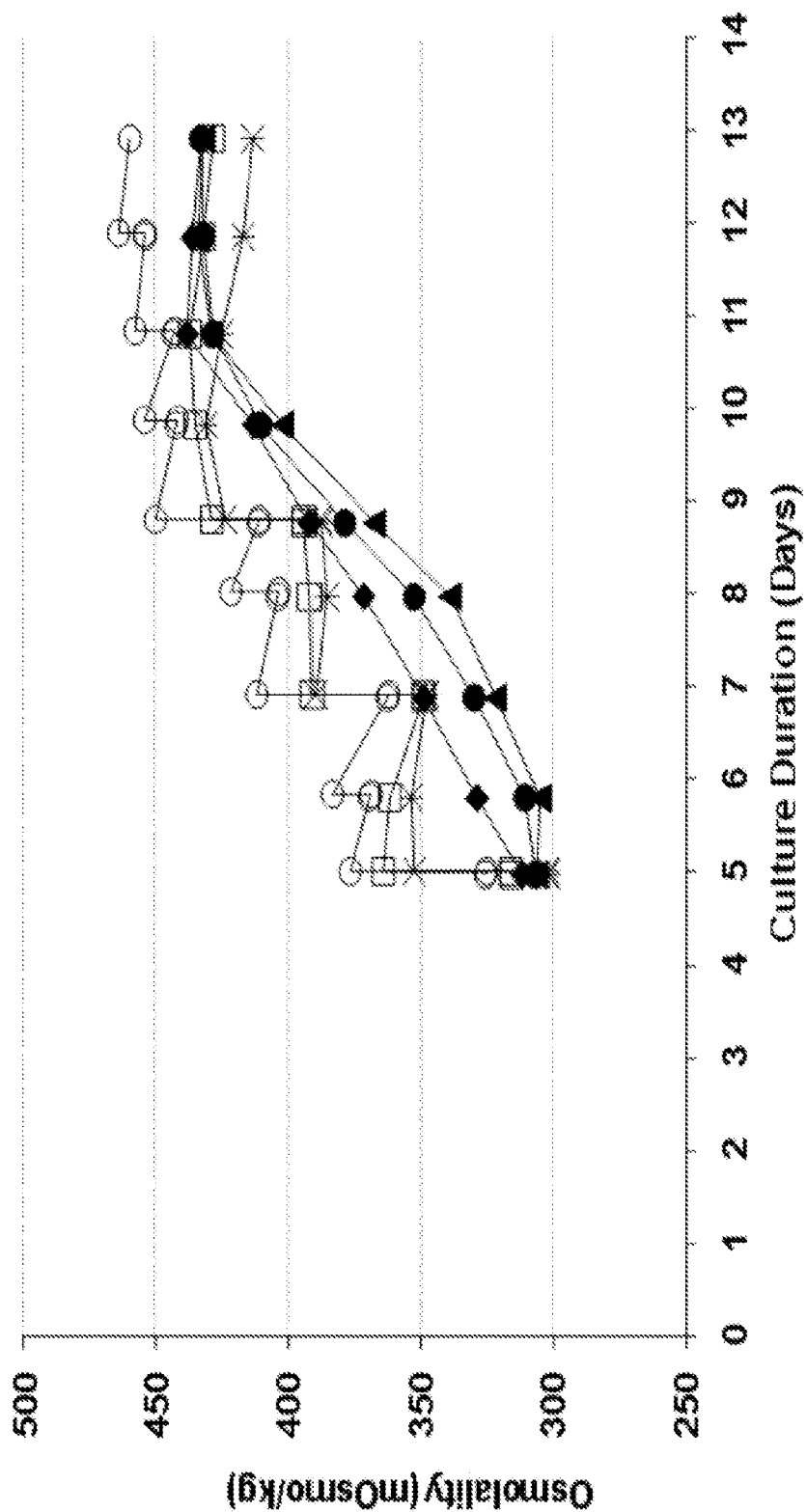

FIG. 4b demonstrates that the continuous feeding runs maintained lower osmolality than the bolus feeding runs. This is likely due to the fact that the continuous glucose feed was designed to feed the culture by the amount required by the cells, rather than simply bolus feeding to a fixed amount every day. The continuous feed may have also lowered the osmolality by allowing nutrient levels to better match the cells' uptake, the cells metabolize nutrients more efficiently and do not experience drastic changes in the environment, as is typically observed in the case of bolus feed.

Figure 4C:
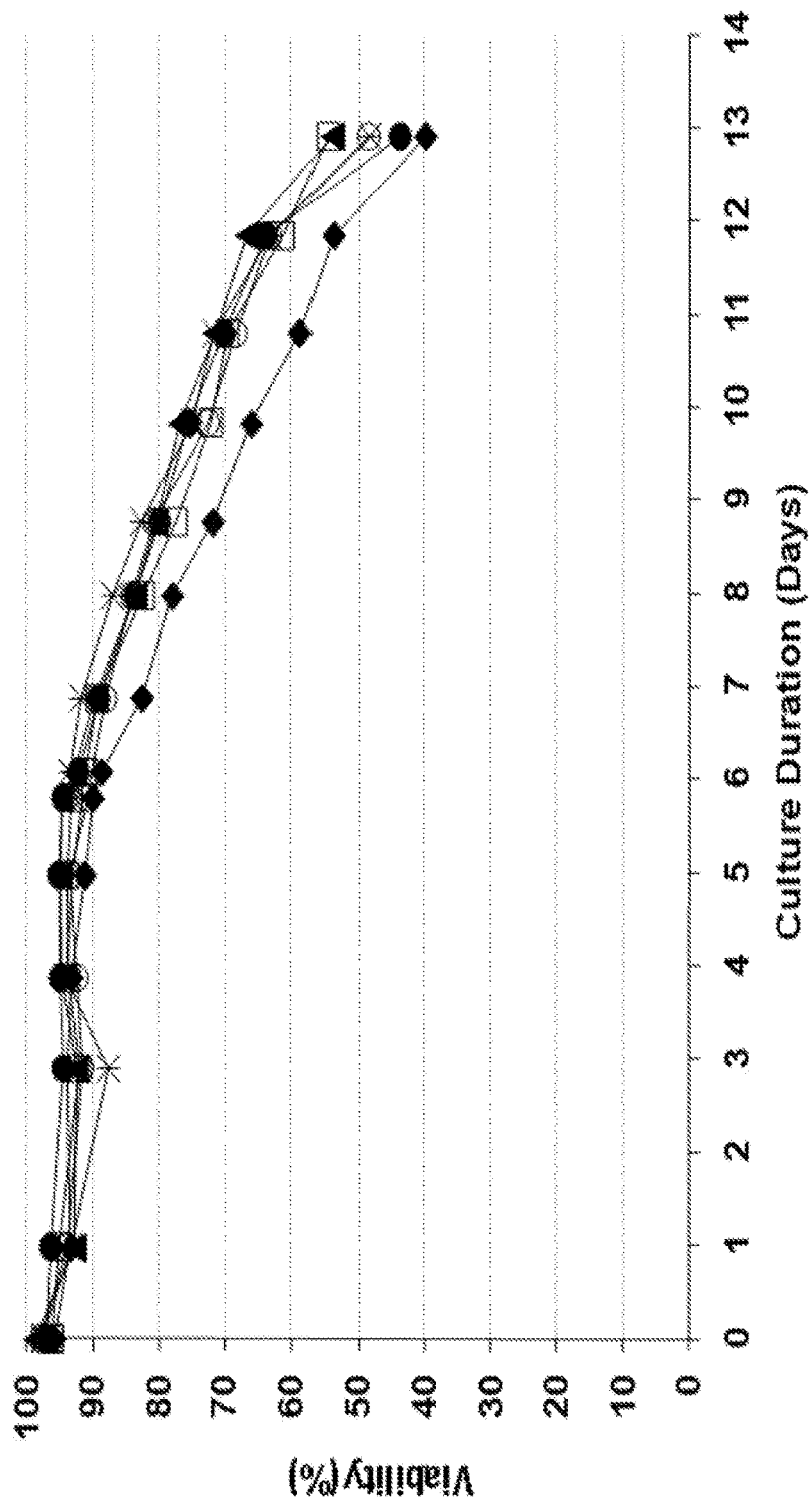
Figure 4D:
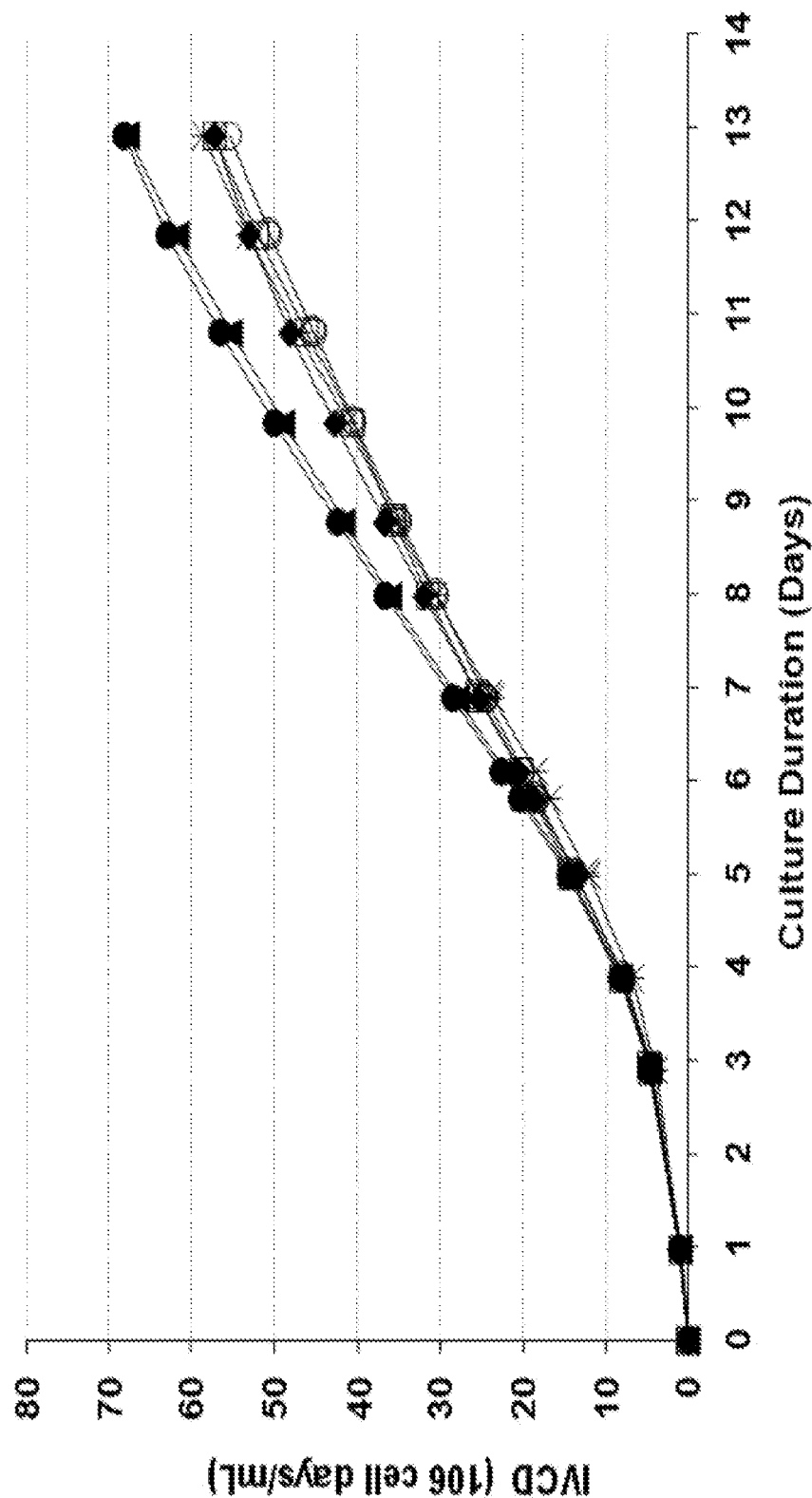

FIG. 4c shows that the cell viability of continuous fed cells is comparable with cells fed using a bolus feeding approach. Although viability of the cells is comparable between the two approaches. FIG. 4d demonstrates that cell density (IVCD) is significantly improved when applying the continuous feed with the continuous glucose. This effect was observed for both runs, solid triangles (▲) and solid circles (●), using two different sets of continuous feed K constants ($K_1$=0.96678, $K_{21}$=−0.00015, $K_{22}$=0.0288) and ($K_1$=0.59499, $K_{21}$=−0.00015, $K_{22}$=0.0348) combined with the same continuous glucose ($K_1$=0.0504, ($K_{21}$=−0.00015, $K_{21}$=0.0331). The continuous feed run represented by solid diamonds (◆), which used the constant feed rate and the same continuous glucose as the other two runs only produced the same IVCD as the bolus feeding run (open circles (○)). This observation implies that the exponential profile of the feed function is better in nutrient delivery for improving cell growth than both the constant feed and bolus feed. The titers for these runs, solid triangle (▲) and solid circle (●), were also the highest among the runs and approximately 7% higher than the control bolus feeding run (open circles (○)). It is possible that, with further optimization of the K constants of the feed function, the titer of the continuous feed can be improved over the bolus feed. It is noted that both the lactate and ammonium profiles of these runs were very similar.

The Continuous Feeding Method as Applied to Cell Line 2

Cell Line 2 was also tested using the continuous feed function. As was done in the study of Cell Line 1, the K values for continuous glucose feeding were determined by fitting the feed function to match actual glucose consumption data generated from bolus feeding runs. The K values for the continuous feed were also derived based on variations of $K_{21}$ and $K_{22}$ from the continuous glucose and $K_1$ was back calculated using the total volume to be delivered within a set time. The control process is 16 days. Bolus glucose was added daily up to 6 Bolus feeds were added on days 5, 7, 9, 11 and 13 at 108 mL each totaling 540 mL of feed. Stated another way, in the dual continuous feeding runs, the continuous glucose feeding K values were kept the same and only the continuous nutrient mixture feeding K values varied.

Figure 5A:
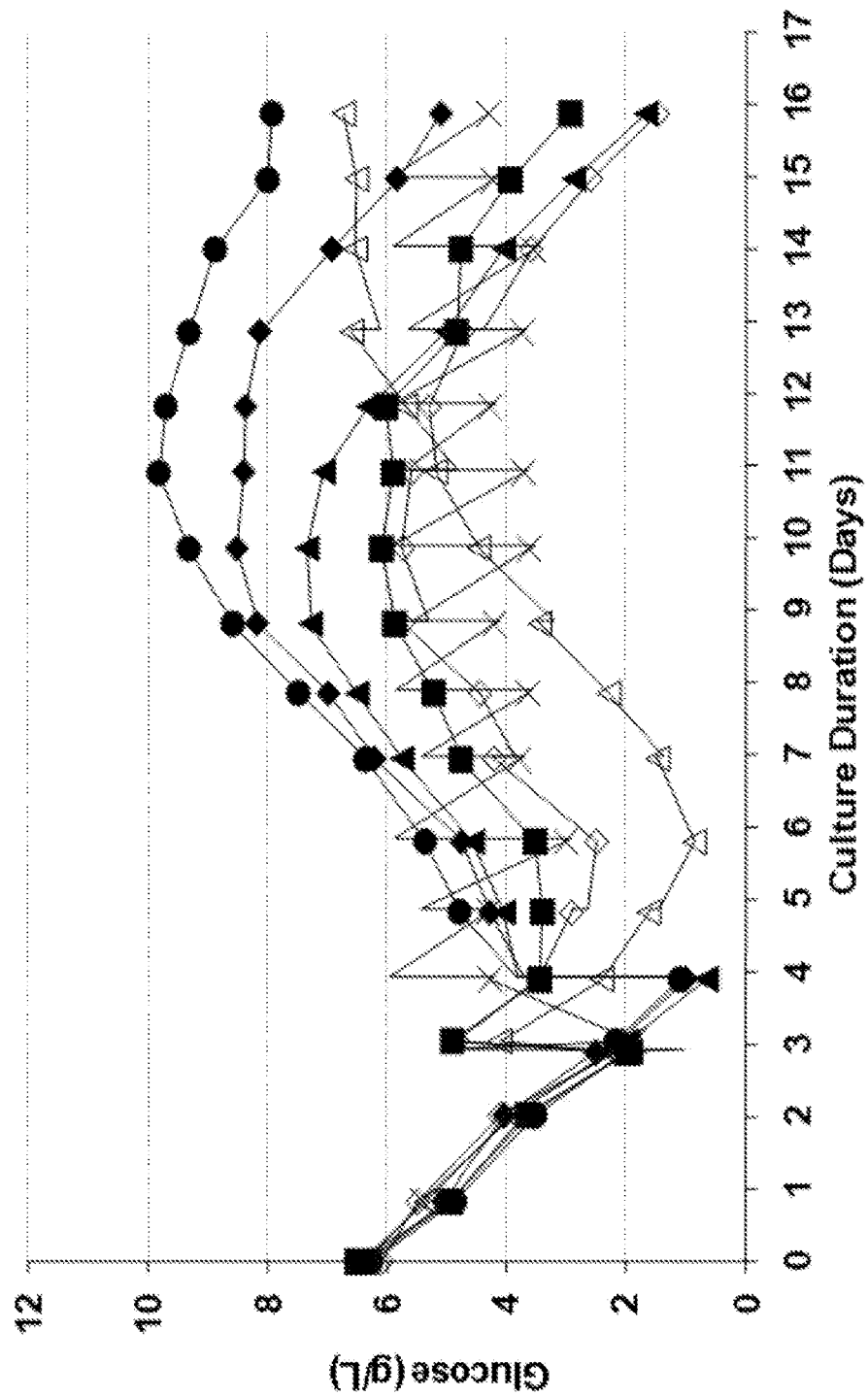
FIGS. 5a-5c are a series of plots related to experiments involving Cell Line 2, and more particularly

FIG. 5 shows the results of the continuous feeding method applied to the Cell Line 2. The two variations of continuous glucose tested were ($K_1$=0.105, $K_{21}$=−0.000051, $K_{22}$=0.0155) and ($K_1$=0.069, $K_{21}$=−0.000048, $K_{22}$=0.018). ($K_1$=0.105, $K_{21}$=−0.000051, $K_{22}$=0.0155) was used for all dual continuous glucose and feed runs. FIG. 5a demonstrates that with empirical development, it is possible to maintain the glucose concentration consistently within a specific range of 3-6 g/L. The run achieving this range is the solid square (■) using continuous glucose ($K_1$=0.105, $K_{21}$=−0.000051, $K_{22}$=0.0155) with continuous feed ($K_1$=2.3821, $K_{21}$=−0.00006, $K_{22}$=0.0092).

Figure 5B:
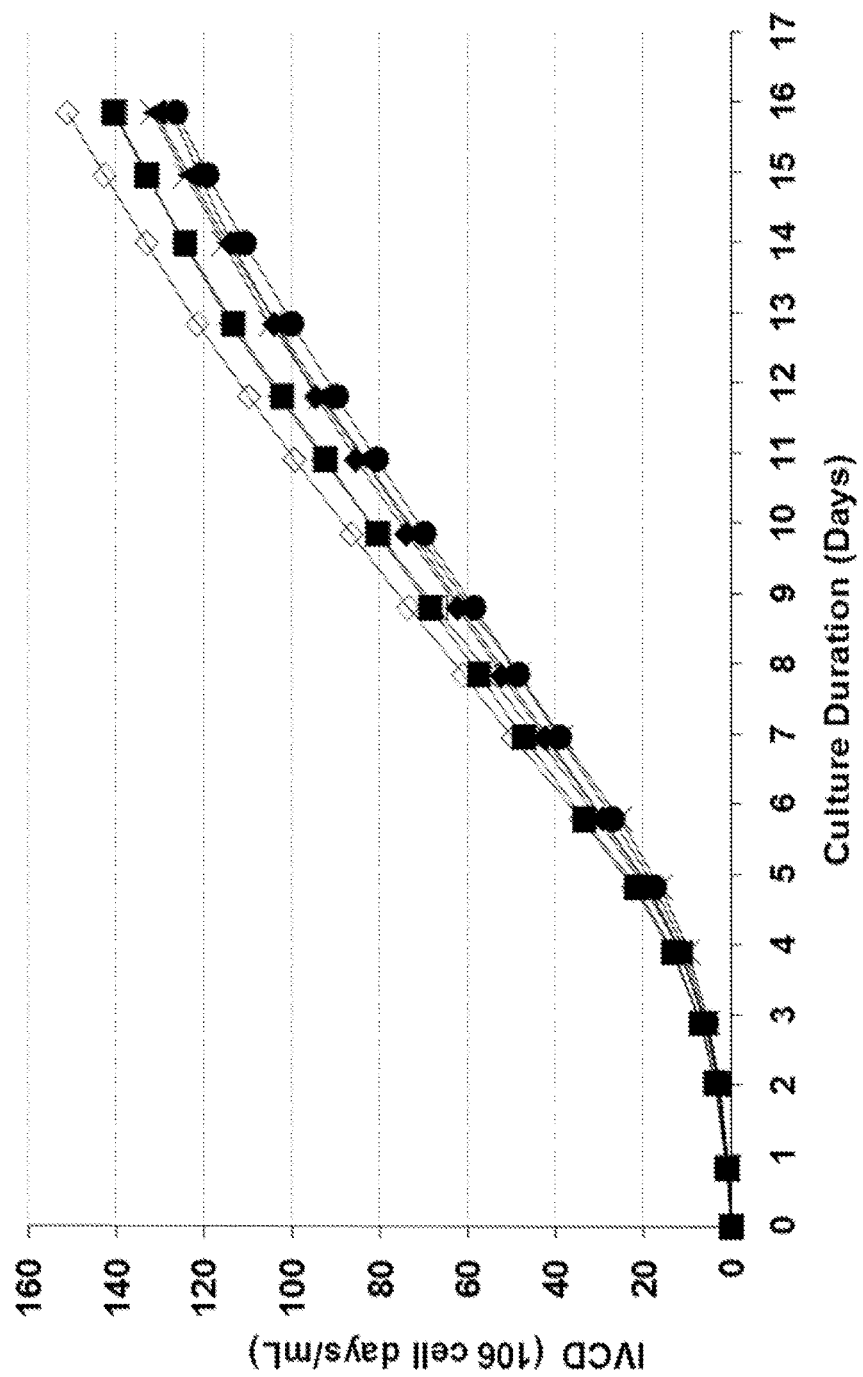

FIG. 5b demonstrates that the cell density (IVCD) of the continuous glucose and bolus feed run (open diamonds (◇)), and the dual continuous glucose and continuous feed run, (solid squares (■)), were significantly improved over the bolus feeding control run (*).

Figure 5C:
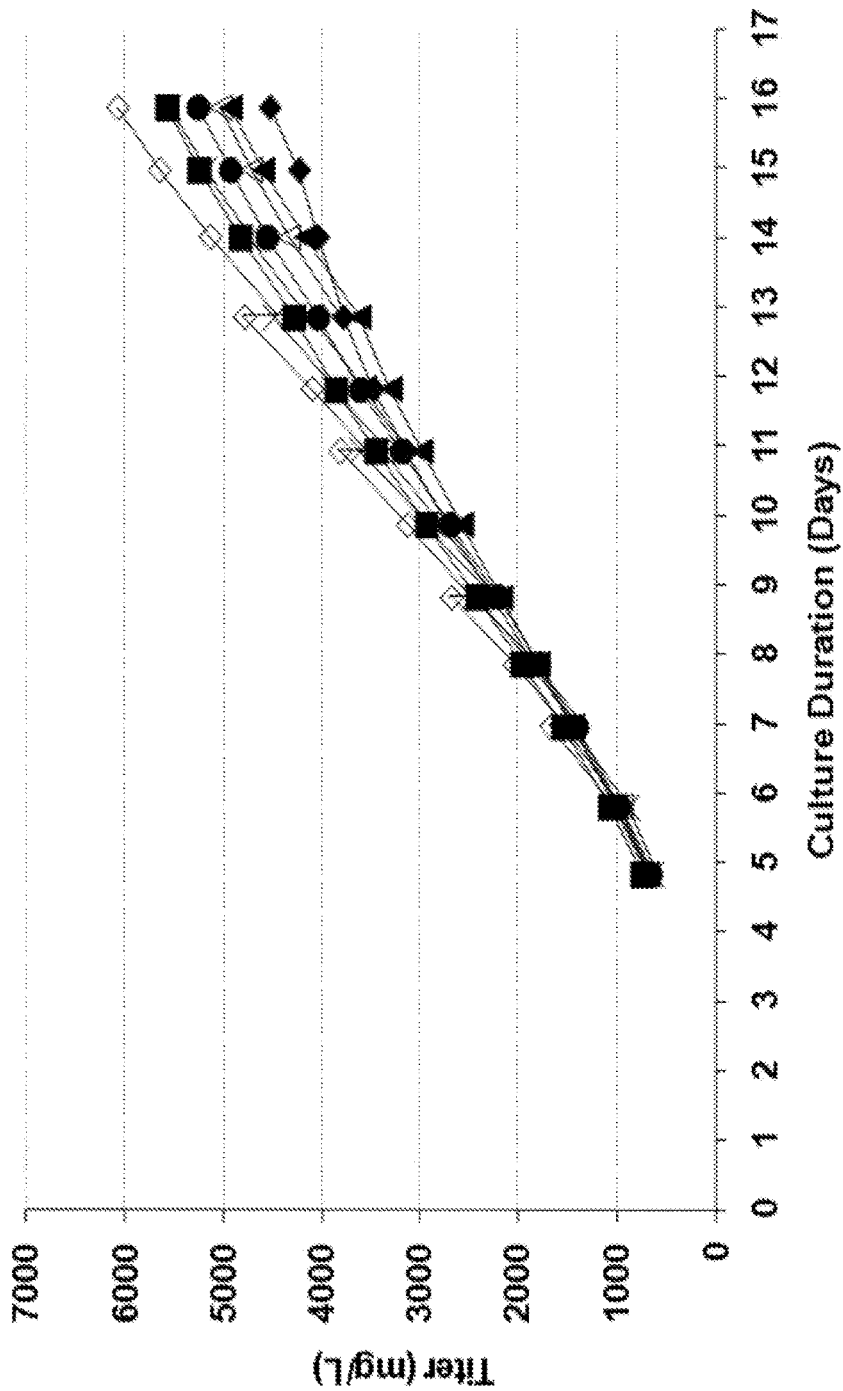

FIG. 5c shows that different continuous feeding functions can produce a wide variation of titers, with some titers being lower and others higher, even though the same amount of feed volume of 540 mL was fed. The run that demonstrated improved titer over bolus feeding was continuous glucose feeding. ($K_1$=0.105, $K_{21}$=−0.000051, $K_{22}$=0.0155) with bolus feed (open diamonds (◇)), the titer of this run was 6 g/L versus the control bolus feeding of 5.5 g/L. Cell viability also varied, with some continuous feeding profiles matching the bolus feeding and some lower. This data shows the range of response with different continuous feeding K values and illustrates the potential for optimization with a range of K values.

Testing Higher Volumes in the Continuous Feed Method Using Cell Line 2

In another experiment, the bolus feed process was changed to 84 mL on days 4 and 5, and 108 mL on days 7, 9, 11 and 13 totaling 600 mL of feed. This modification adds one additional feed day and 60 mL more feed than the previous condition. The K values were further refined for the continuous glucose and continuous feed equations based on the data shown in FIG. 5. The K values for glucose were changed to ($K_1$=0.215, $K_{21}$=−0.000003, $K_{22}$=0.003), which better fit revised glucose consumption data for Cell Line 2. In this study, there were four conditions, as shown in FIG. 6. The first condition (open diamonds (◇)), is the control bolus glucose and feed. The second condition (open triangles (Δ)), is using continuous glucose ($K_1$=0.215. $K_{21}$=−0.000003, $K_{22}$=0.003) coupled with bolus feed. The third condition (solid triangle (▲)), uses the same continuous glucose K values coupled with continuous feed ($K_1$=1.8744, $K_{21}$=−0.000003, $K_{22}$=0.003). The fourth condition (solid diamond (◆)), uses the same continuous glucose K values coupled with continuous feed ($K_1$=2.0827, $K_{21}$=−0.000003, $K_{22}$=0.003). The bolus feed conditions and the fourth condition continuous feed all deliver the same amount of total feed of 600 mL. The third condition continuous feed was set to deliver the previous total of 540 mL for comparison. Despite the volume difference in the third and fourth conditions, the continuous feed trend curves were expected to be the same as both functions share the same $K_{21}$ and $K_{22}$ values. While the $K_{21}$ and $K_{22}$ values remained the same, the $K_1$ value is higher, which commands a higher magnitude of feed rate. In this case, the entire feed curve is shifted higher than the lower $K_1$ feed curve. All the runs have feed delivered within the same timeframe from day 4 through day 13.

In this study, the residual glucose concentration of the continuous glucose was controlled within as tight range of 3-5 g/L for the open triangles (Δ) run. The residual glucose of the dual continuous glucose and feed had more variation but was still acceptable, since its variation was still smaller than the bolus glucose feeding (which had a range of 1-6 g/L).

Figure 6A:
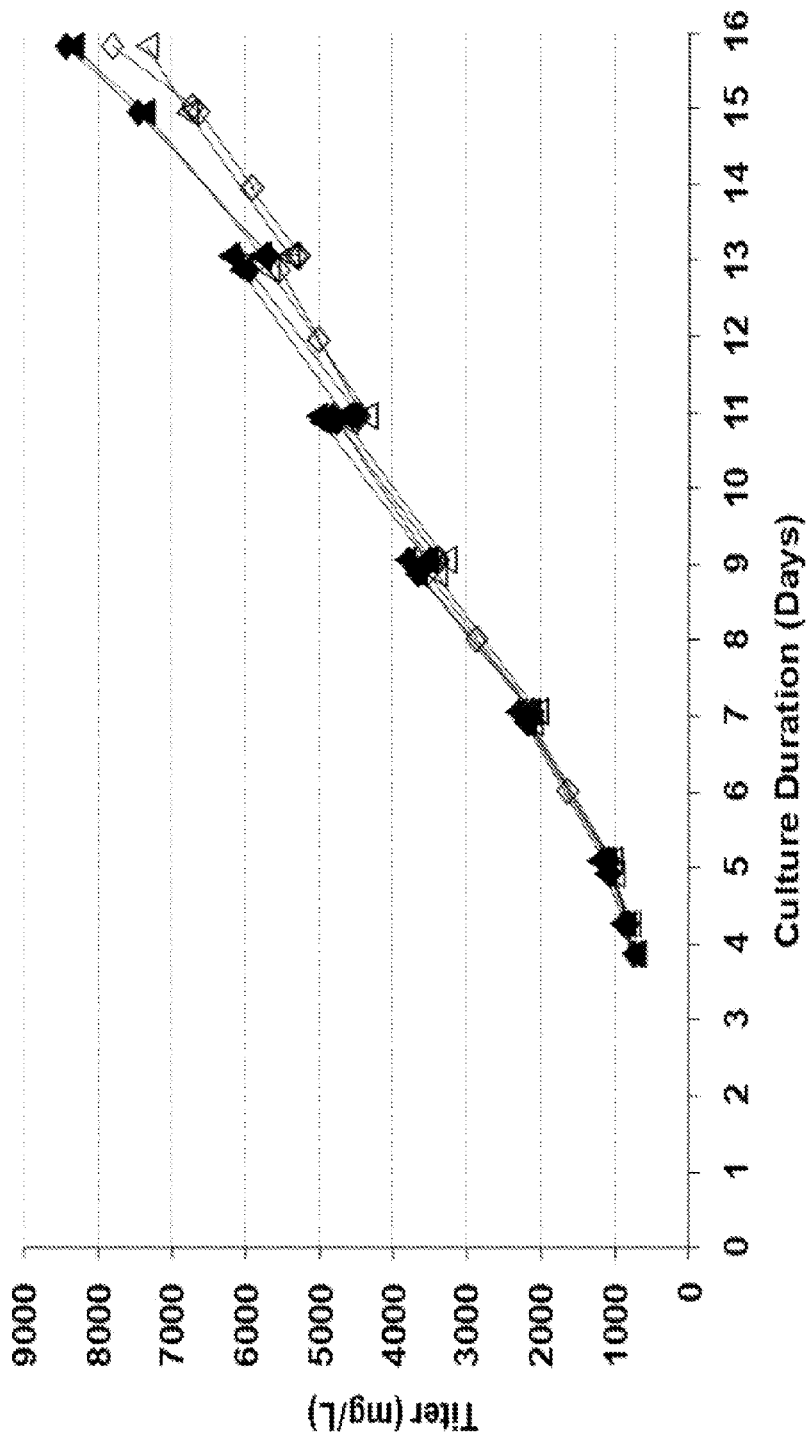
FIGS. 6a-6d are a series of plots related to experiments involving Cell Line 2, and more particularly
Figure 6B:
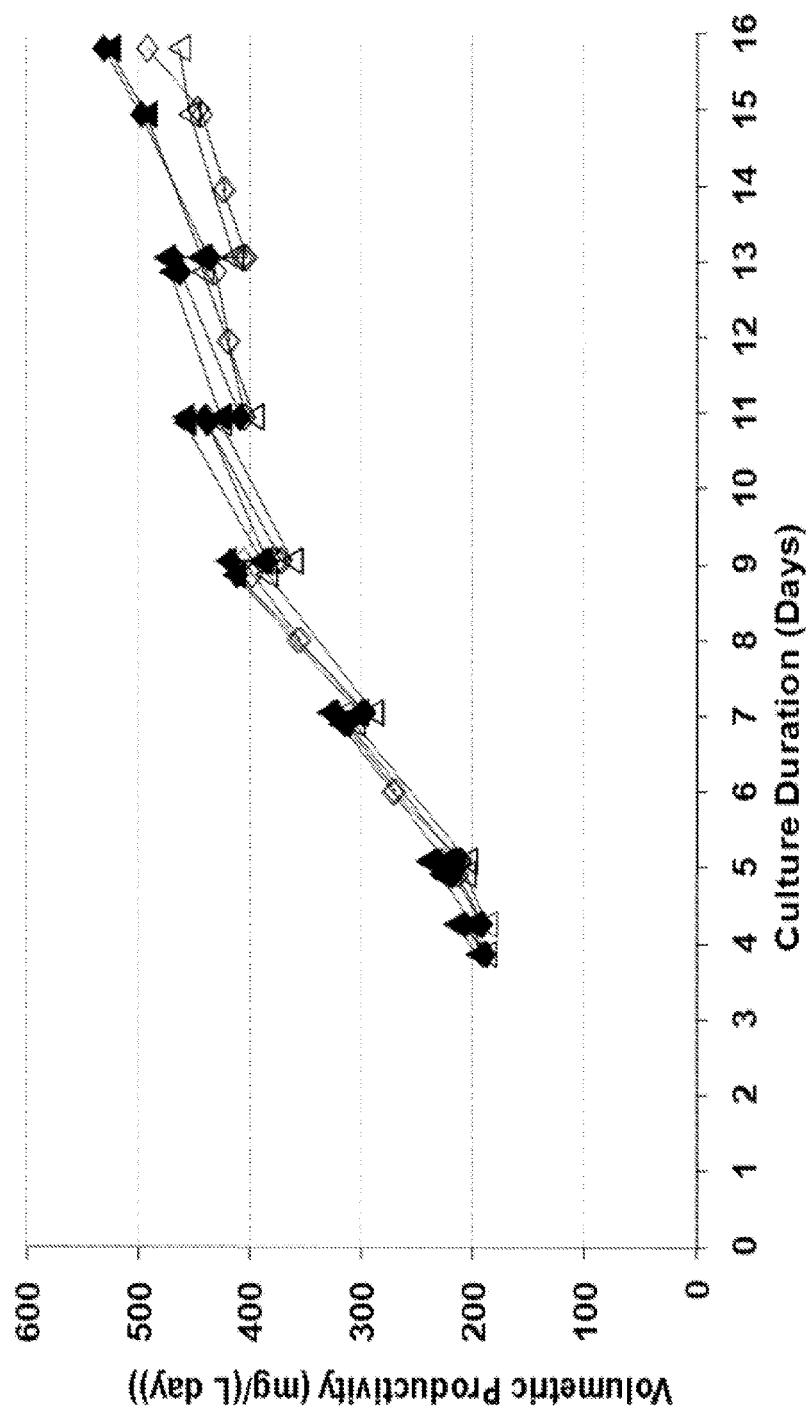

FIG. 6a demonstrates that titer is improved using the continuous glucose coupled with the continuous feed. Both continuous feed conditions reached approximately 8.4 g/L titer, which was the highest titer observed for any Cell Line 2 process. The titer trends of the bolus feed runs were lagging behind the continuous feed runs by as early as day 11. The volumetric productivity was also higher in the continuous feed runs.

Figure 6C:
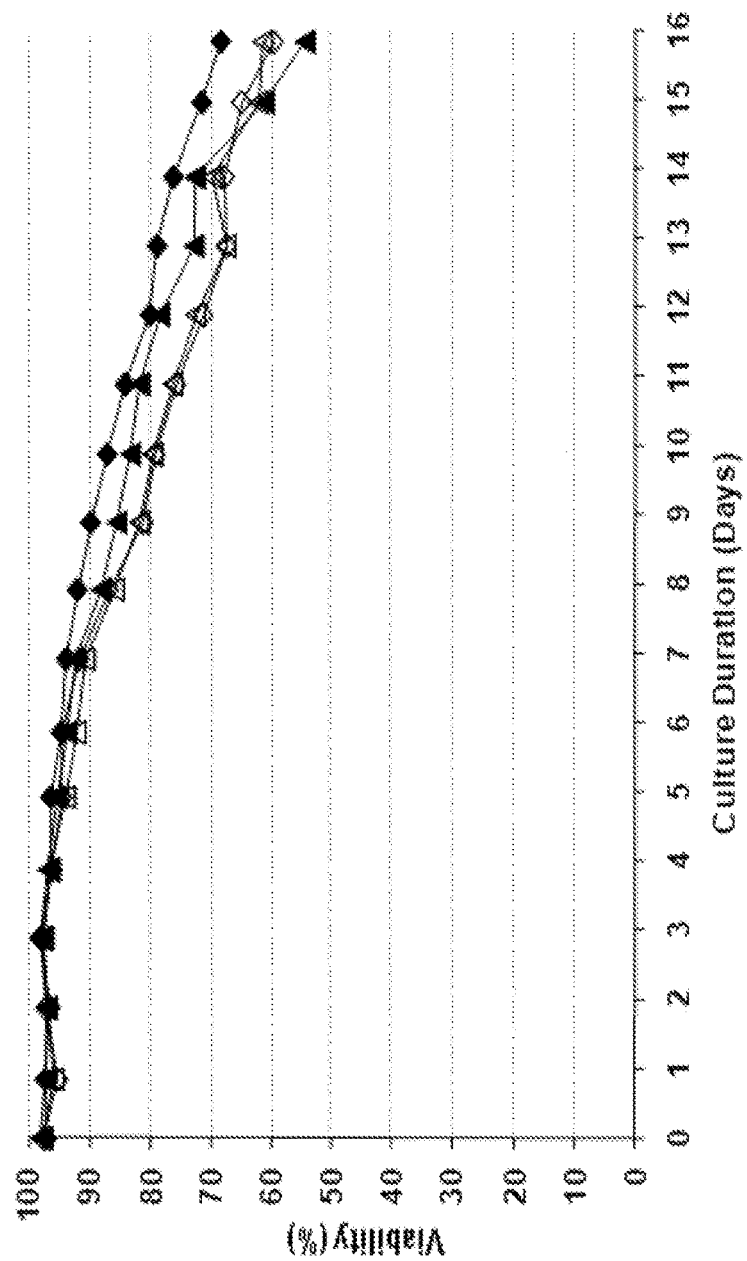
Figure 6D:
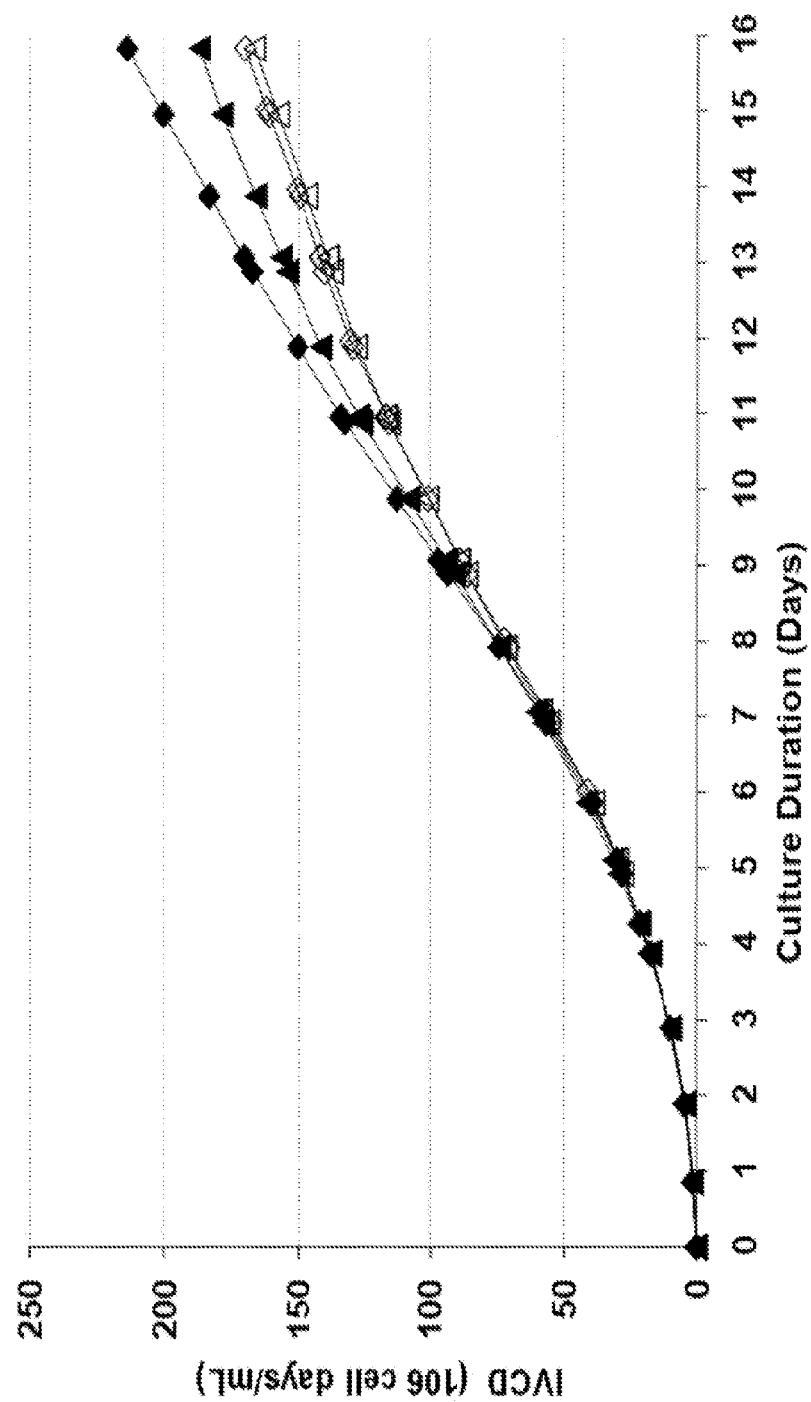

FIG. 6c shows that the cell viability is higher with the continuous feed runs versus the bolus feed runs. In this study the higher continuous feed volume of 600 mL was better than the 540 mL feed volume with respect to cell viability. It was also 9% higher with respect to cell viability than the bolus feeding at the end of production. The same kind of improvement was also observed for the IVCD using the continuous feed delivering 600 mL of feed, as shown in FIG. 6d. At the end of production, this continuous feed reached 214×10$^6$ cell days/mL versus 187×10$^6$ cell days/mL for the 540 mL continuous feed, and 170×10$^6$ cell days/mL for the bolus feeding control. This is approximately 26% improvement in IVCD over the bolus feeding with the best continuous feed.

In continued experiments on the continuous feed volume, two additional variations of the continuous feed were tested in parallel with the control bolus feeding: of 600 mL. The first condition (open circles (○) utilized a continuous feed of ($K_1$=2.6503, $K_{21}$=−0.000003, $K_{22}$=0.003) starting from day 5 and continuing through day 13. Because the continuous feed started a day later than the previous day 4, the total feed was still 600 mL even though the $K_1$ was higher than the previous continuous feed of 2.0827. The $K_{21}$ and $K_{22}$ values were still the same as the previous continuous feed. This condition tests a later continuous feed start while maintaining the same total volume. In the second condition, the continuous feed of ($K_1$=2.2910, $K_{21}$=−0.000003, $K_{22}$=0.003) was tested, which was applied from day 4 through day 13. This is the same start and finish time as the control bolus feeding. The $K_1$ was increased from 2.0827 to 2.2910, however, in order to test the higher total volume of 660 mL. For these two continuous feed conditions, both were coupled with bolus glucose. The objective was to understand the effect of the continuous feed alone without the continuous glucose.

Figure 7A:
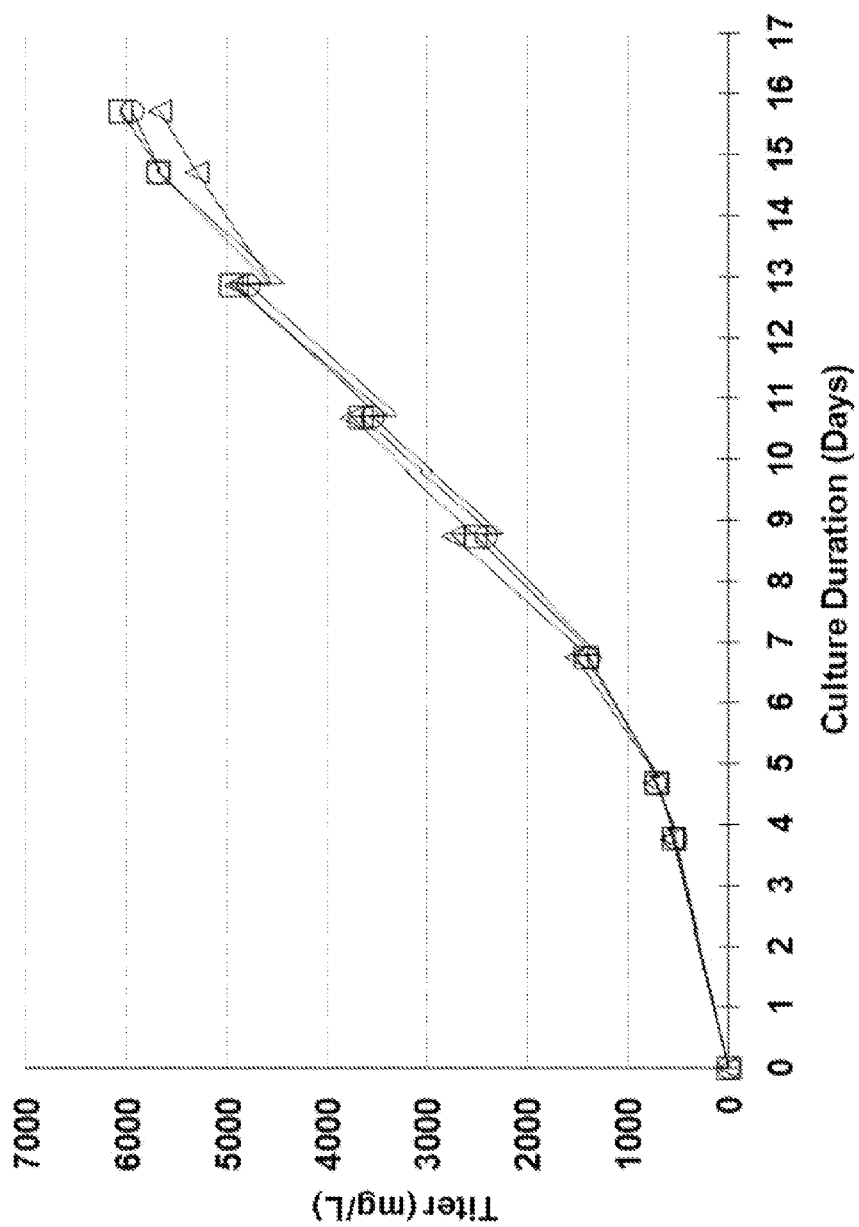
FIGS. 7a-7d are a series of plots related to experiments involving Cell Line 2, and more particularly
Figure 7B:
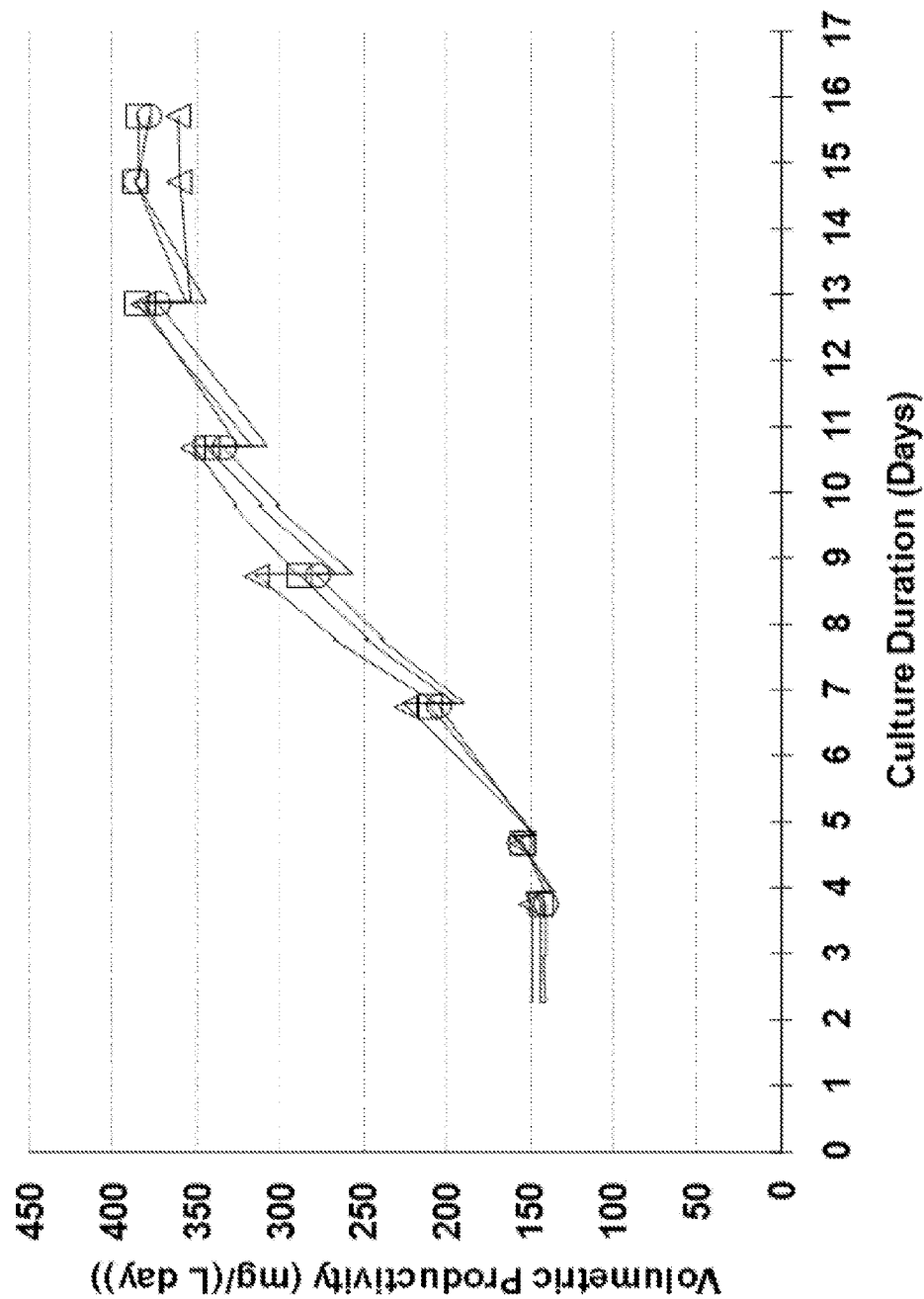
Figure 7C:
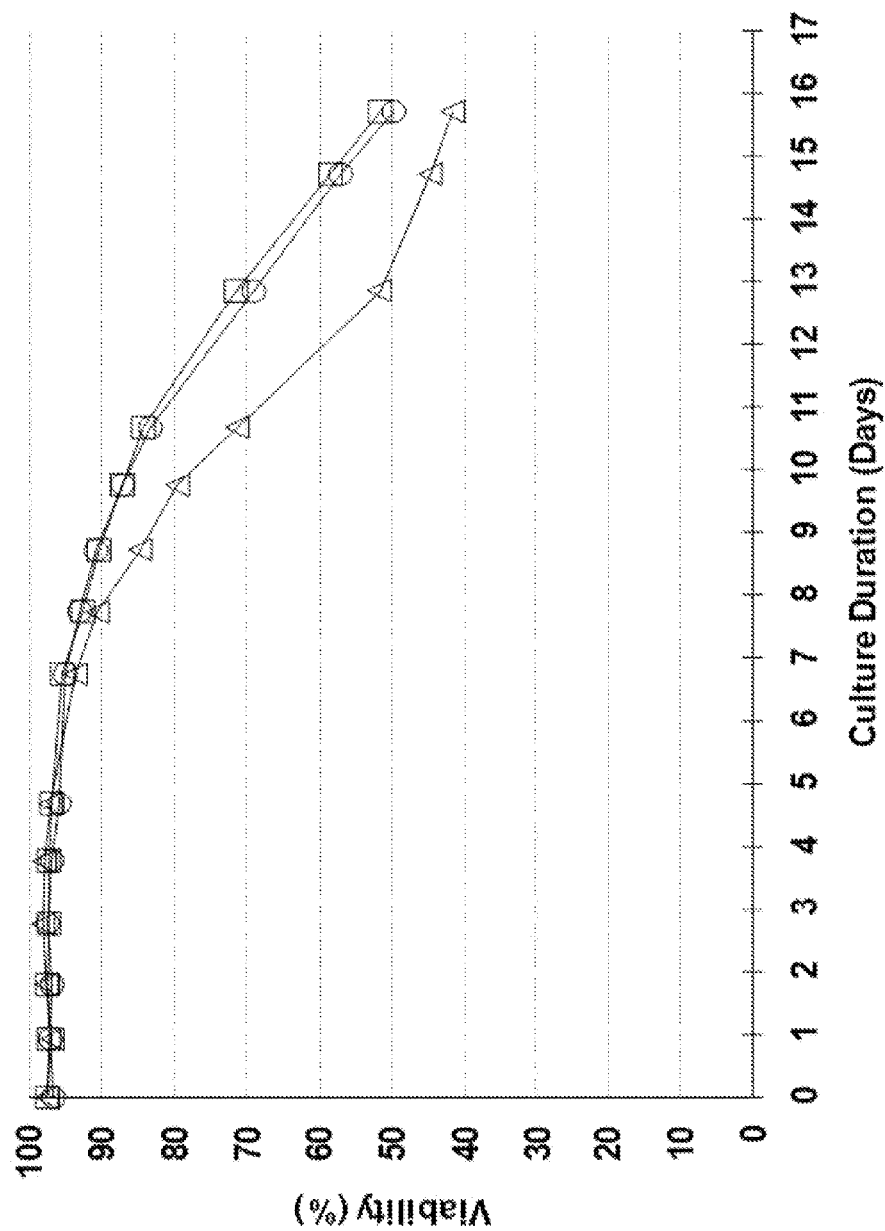
Figure 7D:
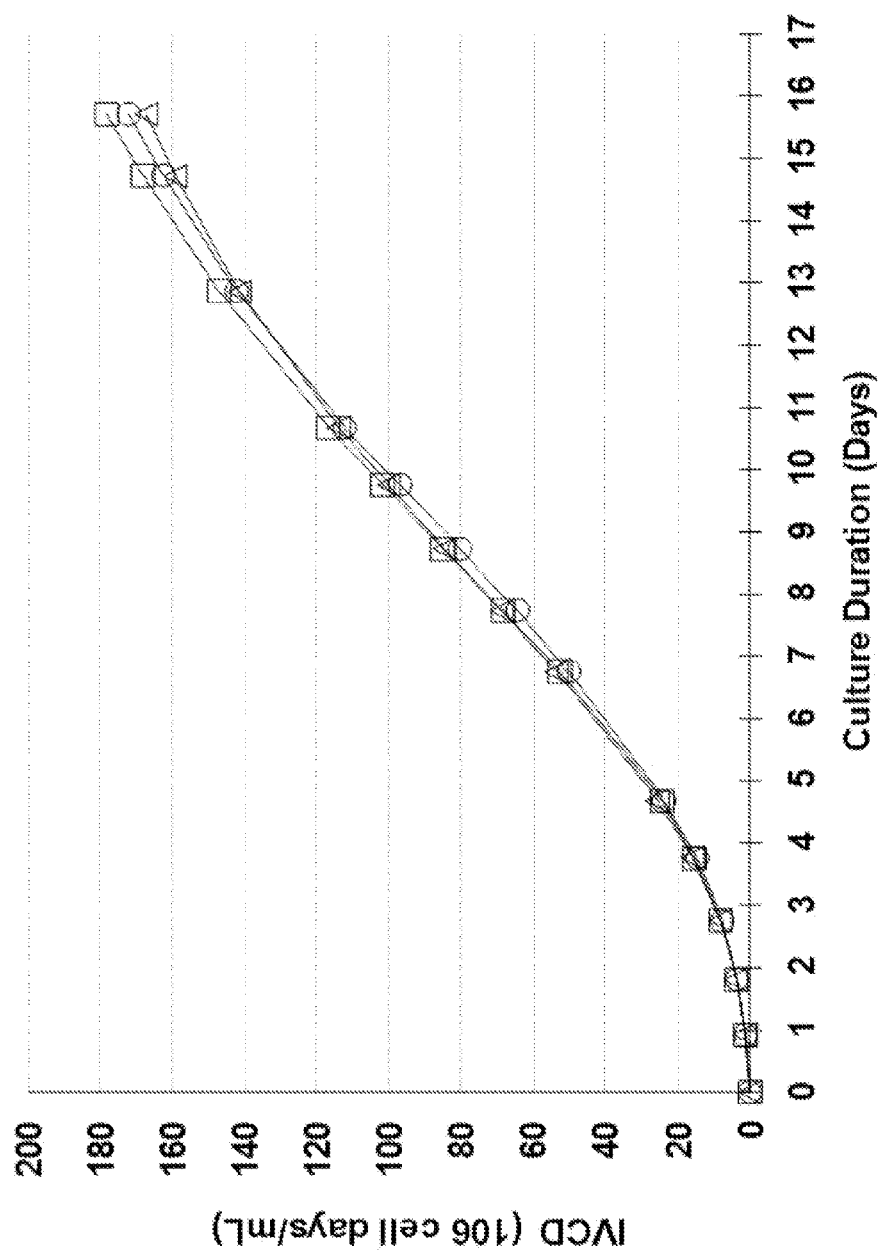

FIGS. 7a and 7b demonstrate that the titer and volumetric productivity were slightly improved with both of the continuous feed conditions. FIG. 7c demonstrates that the viability was significantly improved with the continuous feed conditions. This was previously observed in the conditions of FIG. 6. FIG. 7d demonstrates that the IVCD was only marginally improved with the continuous feed conditions, in contrast to the greater improvement seen in FIG. 5.

Testing the Continuous Feeding Method in Cell Line 3

Cell Line 3 was tested using the continuous feed function. The control bolus feeding process feeds 84 mL on day 4, 108 mL on day 6, and 108 mL on day 8 for a total of 300 mL. The entire process was 12 days. One continuous feed condition coupled with bolus glucose was tested. Without any development, the same $K_{21}$ of −0.000003 and $K_{22}$ of 0.003 from the previous studies using Cell Line 2 were used. The $K_1$ was calculated to be 2.7233 in order to feed 300 mL total starting from day 4 through day 8.

Figure 8A:
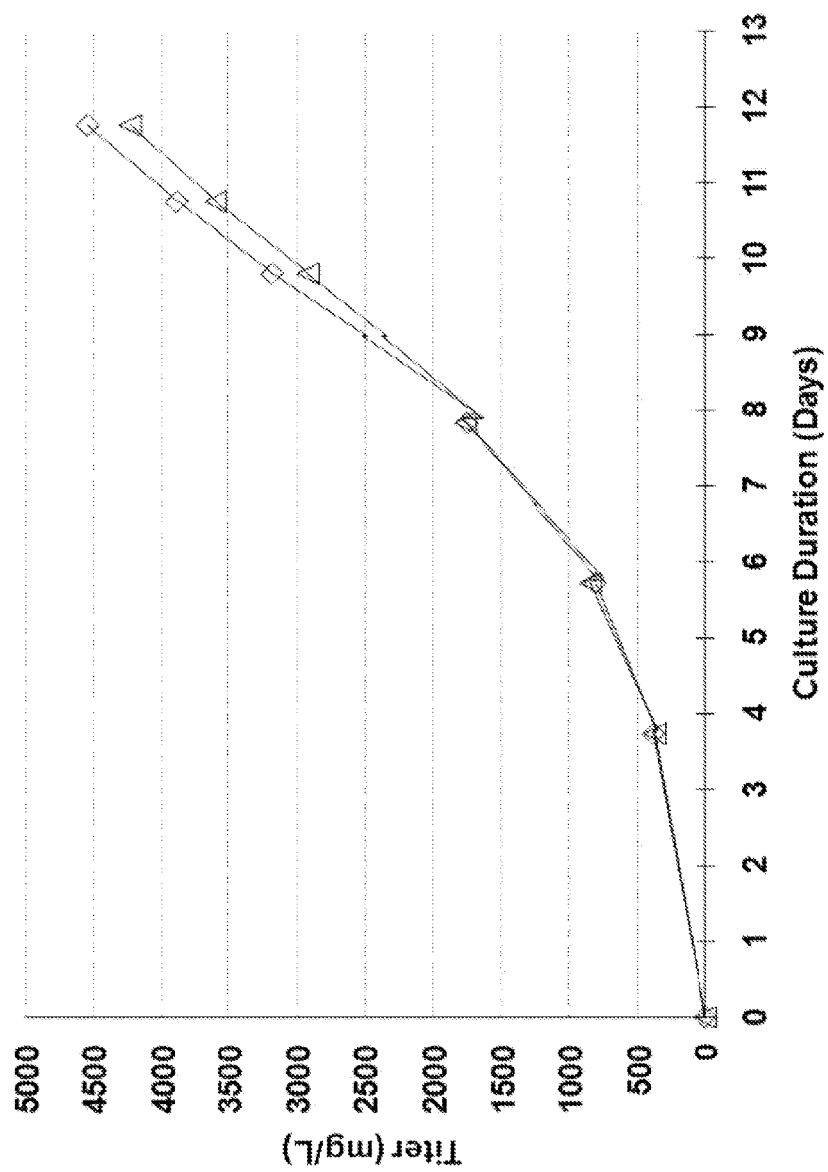
FIGS. 8a-8b are a series of plots related to experiments involving Cell Line 3, and more particularly
Figure 8B:
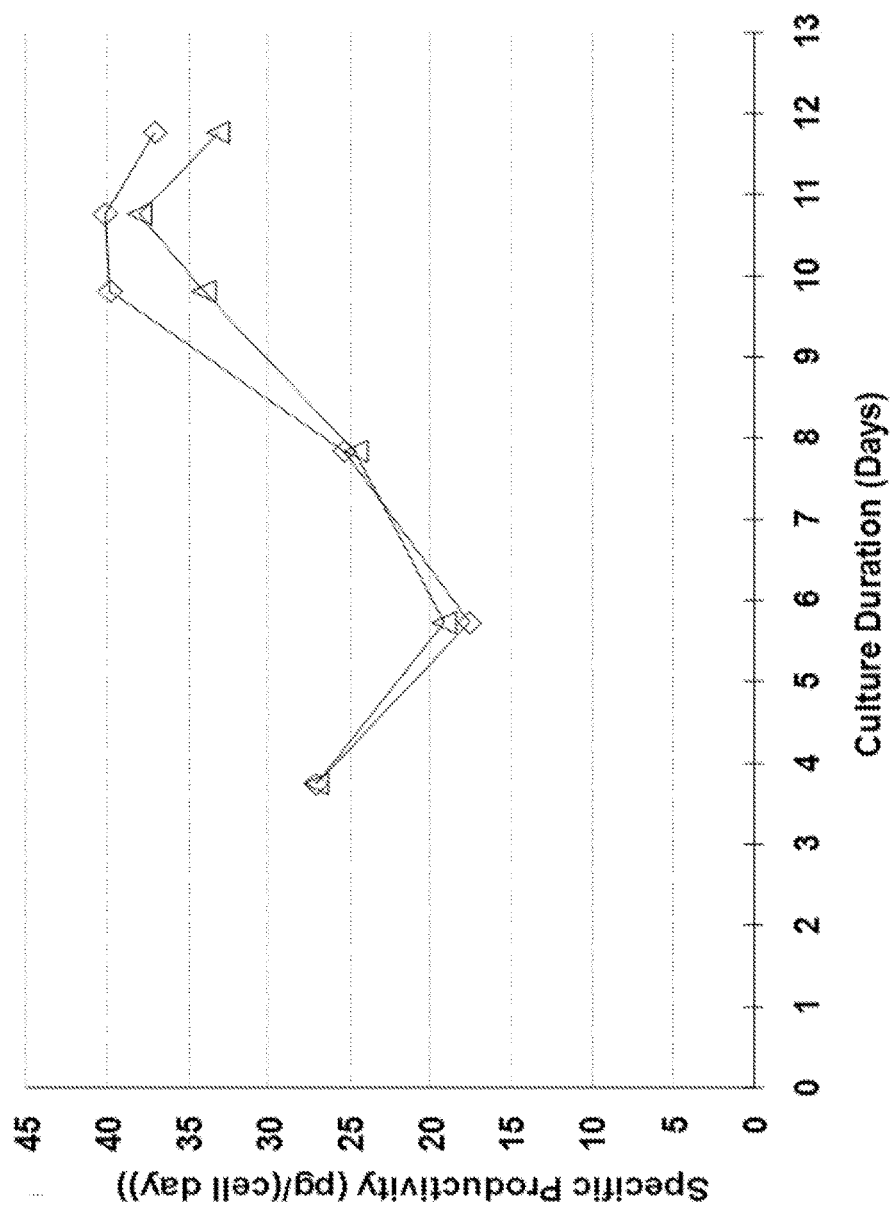

The data for Cell Line 3 showed that the continuous feed improved the titer over the bolus feed from 4.2 g/L to 4.5 g/L (FIG. 8a). The specific productivity, $q_p$, was also higher from day 8 through day 12 with the continuous feed (FIG. 8b). There was no significant difference in cell viability, IVCD, lactate and ammonium profiles. The results demonstrate that the titer for Cell Line 3 can be significantly improved.

Conclusions

The studies with Cell Lines 1, 2 and 3 demonstrate a novel and effective pre-programmed non-feedback continuous feeding model for cell culture that can be successfully applied in place of bolus feeding. Three different, cell lines were tested and various benefits were observed compared to bolus feeding. For Cell Line 1, it was demonstrated that the osmolality profile was lower and the IVCD was higher. For Cell Line 2, it was demonstrated that the titer, volumetric productivity, cell viability and IVCD could all be improved with continuous feeding. With respect to Cell Line 3, it was demonstrated that the titer and specific productivity could be improved with continuous feeding.

In addition to cell culture performance improvement, it was demonstrated that the continuous feeding method can also be used to maintain glucose consistently within a desirable range throughout production. This is desirable and beneficial as it eliminates the need for manual bolus feeding, and consequently eliminates the need for human intervention and conserving resources. Since the continuous feeding method is pre-programmed ahead of a run and operator intervention is eliminated, the process is consistent from run to run with well-developed robust K values. Examples of successful dual continuous glucose and feed runs show that full automation of cell culture feeding is effective.

The results of these studies demonstrate that the disclosed continuous feeding method enhances performance of cell culture growth and protein production, and that the method can replace conventional bolus feeding strategies.

Each reference cited herein is incorporated by reference in its entirety for all that it teaches and for all purposes.

The present disclosure is not to be limited in scope b the specific embodiments described herein, which are intended as illustrations of individual aspects of the disclosure, and functionally equivalent methods and components form aspects of the disclosure. Indeed, various modifications of the disclosure, in addition to those shown and described herein will become apparent to those skilled in the art from the foregoing, description and accompanying drawings. Such modifications are intended to fall within the scope of the appended claims.

What is claimed is:

1. A method of continuously feeding a mammalian cell culture that does not employ feedback control, comprising:
    (a) providing a vessel comprising a mammalian cell culture comprising mammalian cells and media;
    (b) determining preferred values for the consumption rate ($K_1$) of a nutrient, growth rate ($K_{21}$) and growth rate ($K_{22}$) of the cell culture;
    (c) providing an apparatus adapted to impart a continuous feed stream to the cell culture, wherein the apparatus comprises a controller module adapted to continuously feed the culture at a flow rate F, wherein
        F is defined as $K_1 \exp(K_{21} t^2 + K_{22} t)$;
        t is the duration of time from the time the feed stream is added to the bioreactor to the time when the feed stream is stopped; and
        $K_1$, $K_{21}$ and $K_{22}$ are the values determined in (a); and
    (d) activating the controller module to initiate continuous feeding of the cell culture.

2. The method of claim 1, wherein $K_1$, $K_{21}$ and $K_{22}$ are empirically determined.

3. The method of claim 1, wherein $K_1$, $K_{21}$ and $K_{22}$ are modeled.

4. The method of claim 1, wherein the controller module comprises a computer.

5. The method of claim 1, wherein the feed stream comprises multiple nutrients.

6. The method of claim 1, wherein the osmolality of the cell culture remains constant throughout the method.

7. The method of claim 1, wherein the nutrient is glucose.

8. The method of claim 1, wherein the mammalian cell culture is a Chinese Hamster Ovary cell culture.

9. The method of claim 1, wherein the controller module is activated in response to a preselected lactate level in the cell culture.

10. The method of claim 1, wherein the controller module is activated in response to a preselected glucose level in the cell culture.

11. The method of claim 1, wherein the controller module is activated in response to a preselected level of an amino acid.

12. The method of claim 11, wherein the amino acid is asparagine.

13. The method of claim 11, wherein the amino acid is glutamine.

14. The method of claim 1, wherein the feed stream comprises two or more nutrients.

\* \* \* \* \*